US009020581B2

(12) United States Patent
Mahadevan-Jansen et al.

(10) Patent No.: US 9,020,581 B2
(45) Date of Patent: Apr. 28, 2015

(54) SPATIALLY OFFSET RAMAN SPECTROSCOPY OF LAYERED SOFT TISSUES AND APPLICATIONS OF SAME

(75) Inventors: Anita M. Mahadevan-Jansen, Nashville, TN (US); Matthew D. Keller, Kirkland, WA (US); Mark C. Kelley, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 1494 days.

(21) Appl. No.: 12/632,637

(22) Filed: Dec. 7, 2009

(65) Prior Publication Data

US 2010/0145200 A1 Jun. 10, 2010

Related U.S. Application Data

(60) Provisional application No. 61/201,119, filed on Dec. 5, 2008.

(51) Int. Cl.
*A61B 6/00* (2006.01)
*A61B 5/00* (2006.01)
*A61B 17/00* (2006.01)

(52) U.S. Cl.
CPC ............ *A61B 5/4312* (2013.01); *A61B 5/0091* (2013.01); *A61B 2017/00061* (2013.01)

(58) Field of Classification Search
USPC .................................................. 600/476–477
See application file for complete search history.

(56) References Cited

U.S. PATENT DOCUMENTS

| 5,348,018 | A  | * | 9/1994  | Alfano et al. ................. 600/476 |
|---|---|---|---|---|
| 2001/0041843 | A1 | * | 11/2001 | Modell et al. ................. 600/473 |
| 2006/0036181 | A1 | * | 2/2006  | Treado et al. ................. 600/476 |
| 2006/0155195 | A1 | * | 7/2006  | Maier et al. ................... 600/476 |
| 2008/0076985 | A1 | * | 3/2008  | Matousek et al. ............ 600/310 |
| 2009/0086202 | A1 | * | 4/2009  | Wang et al. ................... 356/301 |
| 2010/0106025 | A1 | * | 4/2010  | Sarfaty et al. ................ 600/476 |

OTHER PUBLICATIONS

P. Matousek et al., Subsurface probing in diffusely scattering media using spatially offset Raman spectroscopy, Appl. Spectrosc., Nov. 4, 2005, p. 393-400, vol. 59.
N. A. Macleod et al., Prediction of sublayer depth in turbid media using spatially offset Raman spectroscopy, Analytical chemistry, Nov. 1, 2008, p. 8146-8152, vol. 80, No. 21.
B. Krishnapuram et al., Sparse multinomial logistic regression: Fast algorithms and generalization bounds, IEEE Transactions on Pattern Analysis and Machine Intelligence, Jun. 2005, p. 957-968, vol. 27, No. 6.
C. M. Krishna et al., Raman spectroscopy of breast tissues, Expert Rev. of Mol. Diagn., Mar. 2008, p. 149, 8.2.

(Continued)

*Primary Examiner* — Unsu Jung
*Assistant Examiner* — Shahdeep Mohammed
(74) *Attorney, Agent, or Firm* — Morris Manning & Martin LLP; Tim Tingkang Xia, Esq.

(57) ABSTRACT

The present invention in one aspect relates to a method for surgical margin evaluation of tissues during breast conserving therapy at a surgical site of interest. In one embodiment, the method comprises the steps of acquiring a plurality of spatially offset Raman spectra from the surgical site of interest, identifying tissue signatures from the plurality of spatially offset Raman spectra, and determining surgical margins of the surgical site from the identified tissue signatures.

22 Claims, 15 Drawing Sheets

(56) References Cited

OTHER PUBLICATIONS

A. S. Haka et a., In vivo margin assessment during partial mastectomy breast surgery using raman spectroscopy, Cancer Res., Mar. 15, 2006, p. 3317-3322, vol. 66, No. 6.

E. B. C. T. C. Group, Effects of radiotherapy and surgery in early breast cancer. An overview of the randomized trials, N. Engl. J. of Med., Nov. 30, 1995, p. 1444-1455, vol. 333, No. 22.

G. C. Balch et al., Accuracy of intraoperative gross examination of surgical margin status in women undergoing partial mastectomy for breast malignancy, Am. Surg., 2005, p. 22-27, discussion 27-28, vol. 71, No. 1.

N. Cabioglu et al., Role for intraoperative margin assessment in patients undergoing breast-conserving surgery, Ann. of Surg. Oncol., 2007, p. 1458-1471, vol. 14, No. 4.

L. M. Moreira et al., Raman spectroscopy: A powerful technique for biochemical analysis and diagnosis, Spectr.-Int. J., 2008, p. 1-19, vol. 22.

B. H. Yeap et al., Specimen shrinkage and its influence on margin assessment in breast cancer, Asian journal of surgery, Jul. 2007, p. 183-187, vol. 30, No. 3.

N. Stone et al., Subsurface probing of calcifications with spatially offset Raman spectroscopy (SORS): future possibilities for the diagnosis of breast cancer, Analyst, 2007, p. 899-905, vol. 132.

M. V. Schulmerich et al., Transcutaneous fiber optic Raman spectroscopy of bone using annular illumination and a circular array of collection fibers, Journal of biomedical optics, Nov./Dec. 2006, p. 060502, vol. 11, No. 6.

P. Matousek et al., Noninvasive Raman spectroscopy of human tissue in vivo, Appl. Spectrosc., 2006, p. 758-763, vol. 60, No. 7.

S. K. Majumder et al., Comparison of autofluorescence, diffuse reflectance, and Raman spectroscopy for breast tissue discrimination, J. of Biomed. Optics, 2008, p. 054009, vol. 13, No. 5.

M. D. Keller et al., Raman spectroscopy for cancer diagnosis, Spectroscopy, Nov. 1, 2006, p. 33-41, vol. 21.

U. Utzinger et al., Fiber optic probes for biomedical optical spectroscopy, J. Biomed. Opt., Jan. 2003, p. 121-147, vol. 8, No. 1.

M. D. Keller et al., Spatially offset Raman spectroscopy of layered soft tissues, Opt. Lett., Apr. 1, 2009, p. 926-928, vol. 34, No. 7.

M. D. Keller et al., Numerical simulations of spatially offset Raman spectroscopy for breast tumor margin analysis, Applied Spectroscopy, 2010, p. 607-614, vol. 64, No. 6, Optics express (in preparation).

C. A. Lieber et al., Automated method for subtraction of fluorescence from biological Raman spectra, Appl. Spectrosc., 2003, p. 1363-1367, vol. 57, No. 11.

\* cited by examiner

SPATIALLY OFFSET RAMAN SPECTROSCOPY OF LAYERED SOFT TISSUES AND APPLICATIONS OF SAME

CROSS-REFERENCE TO RELATED PATENT APPLICATION

This application claims priority to and the benefit of, pursuant to 35 U.S.C. §119(e), U.S. provisional patent application Ser. No. 61/201,119, filed Dec. 5, 2008, entitled "SPATIALLY OFFSET RAMAN SPECTROSCOPY OF LAYERED SOFT TISSUES AND APPLICATIONS OF SAME," by Anita M. Mahadevan-Jansen, Matthew D. Keller and Mark C. Kelley, the content of which is incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference. In terms of notation, hereinafter, "[n]" represents the nth reference cited in the reference list. For example, [2] represents the 2nd reference cited in the reference list, namely, M. D. Keller, E. M. Kanter, and A. Mahadevan-Jansen, "Raman spectroscopy for cancer diagnosis," Spectroscopy 21, 33-41 (2006).

STATEMENT OF FEDERALLY-SPONSORED RESEARCH

This invention was made with government support awarded by the National Institutes of Health of the United States under Contract No. 5P50 CA098131-03, and by the Department of Defense of the United States under Contract No. W81XWH-09-1-0037. The government has certain rights to this invention.

FIELD OF THE INVENTION

The present invention generally relates to spatially offset Raman spectroscopy of soft tissues, and more particularly to a system and method that utilizes spatially offset Raman spectroscopy (SORS) for surgical margin evaluation during breast conserving therapy and discriminating two layers of soft tissues.

BACKGROUND OF THE INVENTION

Most of the approximately 180,000 patients diagnosed with early-stage invasive breast cancer or carcinoma in situ have the option of breast conserving therapy (BCT), a procedure that provides superior cosmetic results compared with total mastectomy [9]. This method of treatment involves a lumpectomy, or the local removal of the primary breast lesion with clear tumor-free margins, typically followed by radiotherapy for optimal management of the disease. Several prospective, randomized studies demonstrate no difference in the 10-year survival of patients undergoing successful BCT versus total mastectomy, making it a viable option for many patients. It has been shown that the presence of tumor in the removed tissue within 1-2 mm of the surgical margin is strongly correlated with the risk of local recurrence. Margins therefore play a key role in the prognosis of the patient with respect to local recurrence of breast cancer and are directly correlated to the success of BCT as a treatment modality. Consequently, there is a need for intraoperative evaluation of the resection front so that immediate re-excision of suspicious margins can be performed, minimizing the necessity for a second surgery down the line.

Any method used to evaluate the surgical margins must be rapid and relatively simple to implement if it is to be used in routine clinical care. The simplest technique for determining margin status is based on visual inspection of the excised tissue for evidence of tumor, a method that leads to incorrect diagnoses, and therefore repeat surgeries or a higher risk of recurrence, in at least 25% of cases. Serial sectioning with standard histopathology provides a definitive diagnosis of margin status, but results may take several days to over a week, meaning the patient will go through a period of uncertainty and then require a second procedure if tumor-positive margins are found. Among intraoperative techniques, frozen section pathology is commonly used but is time consuming and prone to sampling error. Imprint cytology ("touch prep") and ultrasound are more accurate than gross examination, but they can be time consuming and have limited sensitivity. Current intraoperative margin evaluation techniques all have significant limitations in accuracy and/or time required [10, 11]. These limitations in current methods emphasize the continued need for a real-time, intraoperative tool that can accurately determine the status of breast surgical margins.

Light based methods have the potential to provide automated, fast determination of surgical margin status of the excised specimen while the patient is still in the operating room without disrupting or removing any tissue for such analysis. Although several techniques have been used to investigate breast pathology, including diffuse optical tomography and optical coherence tomography, these techniques have limited applicability in surgical margin evaluation due to their trade-off between resolution and penetration depth, and/or method of contrast. Fluorescence and reflectance spectroscopy have been thoroughly researched for breast cancer diagnosis, but these techniques suffer from lower sensitivity than desired.

Several groups have successfully applied Raman spectroscopy for disease detection, particularly for cancer diagnosis in various epithelial tissues [1-3]. A review of the use of Raman spectroscopy for breast cancer diagnosis are reported by Krishna et al. [12]. The inventors have also conducted a study in which nearly 300 Raman spectra from in vitro breast samples were classified into four histopathological categories with 99% overall accuracy [13], which objectively demonstrates the superiority of Raman spectroscopy for this purpose versus diffuse reflectance and/or autofluorescence. A study on guiding resection with Raman spectroscopy was reported [14]. But it relies on a standard fiber probe configuration and does not consider the need for determining margin status to a depth of 1-2 mm on the excised specimen. All of the studies is focused on diagnosis of breast cancer and not for guidance of therapy or margin assessment.

Therefore, a heretofore unaddressed need still exists in the art to address the aforementioned deficiencies and inadequacies.

SUMMARY OF THE INVENTION

In one aspect, the present invention relates to a method for surgical margin evaluation of tissues at a surgical site of interest. In one embodiment, the method includes the steps of acquiring a plurality of spatially offset Raman spectra from the surgical site, identifying tissue signatures from the plurality of spatially offset Raman spectra, and determining surgical margin status of the surgical site from the identified tissue signatures.

In one embodiment, the acquiring step comprises the step of illuminating the surgical site at least one first spot with light. The light in one embodiment is a coherent light generated from a laser.

The acquiring step further comprises the step of collecting Raman scattering light from the surgical site at a plurality of second spots, respectively, in response to illumination by the light, where each second spot is apart from the at least one first spot so as to define a source-detection (S-D) offset distance between the at least one first spot illuminated with the light and the second spot from which the Raman scattering light is collected. In one embodiment, the S-D offset distance is smaller than 50 mm.

The acquiring step further comprises the step of obtaining the plurality of spatially offset Raman spectra from the collected Raman scattering light, wherein each spatially offset Raman spectrum is corresponding to a respective second spot of the surgical site, and associated with a depth of the tissues at which the Raman light is scattered. In one embodiment, the obtaining step is performed with at least one of a spectrograph and a CCD camera.

The acquiring step is performed with a probe having a working end and in-line filters placed on the working end. In one embodiment, the probe comprises at least one first fiber positioned over the at least one first spot of the surgical site for delivering the light thereto, and at least one second fiber positioned over the surgical site and translationally movable from one to another of the plurality of second spots for collecting the Raman scattering light therefrom. In another embodiment, the probe comprises at least one first fiber positioned over the at least one first spot of the surgical site for delivering the light thereto, and a plurality of second fibers spatially arranged surrounding the at least one first fiber, each second fiber adapted for collecting the Raman scattering light from a corresponding second spot. In yet another embodiment, the probe comprises a fiber array having at least one first fiber, and a plurality of second fibers, where the at least one first fiber and the plurality of second fibers spatially arranged in a row or in a matrix form, the at least one first fiber is adapted for delivering the light to the at least one first spot of the surgical site, and the plurality of second fibers is adapted for collecting the Raman scattering light from the plurality of second spots of the surgical site. In one embodiment, the probe comprises a fiber array having at least one first fiber, and a plurality of second fibers spatially arranged in a radial ring form originated from the at least one first fiber, where the at least one first fiber is adapted for delivering the light to the at least one first spot of the surgical site, and the plurality of second fibers is adapted for collecting the Raman scattering light from the plurality of second spots of the surgical site.

The method further comprises the step of acquiring a Raman spectrum from the at least one first spot illuminated with the light.

In one embodiment, the identifying step comprises the step of comparing each of the Raman spectrum acquired from the at least one first spot and the plurality of spatially offset Raman spectra with a standard Raman spectrum of tumor tissues so as to determine a tumor signature of the corresponding Raman spectrum. The identifying step is performed with a chemometric or other statistical techniques to determine the surgical margin status and/or size of the negative margin, wherein the statistical chemometrics method including a spare-multinomial linear regression and/or the classical least squares (CLS) method. Furthermore, the identifying step comprises the steps of (a) identifying spectral peaks of one of the plurality of spatially offset Raman spectra at a corresponding S-D offset distance, (b) calculating the tumor signature, $\{T(i)\}$, for each identified peak of the one of the plurality of spatially offset Raman spectra at the corresponding S-D offset distance $$T(i)=[I_{SD}(i)-I_N(i)]/[I_{tumor}(i)-I_N(i)],$$

where $i=1, 2, \ldots, N$, N being the number of the spectral peaks, $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively, (c) averaging the tumor signature $\{T(i)\}$ for the N spectral peaks of the one of the plurality of spatially offset Raman spectra to obtain an overall relative tumor contribution in the one of the plurality of spatially offset Raman spectra, and (d) repeating steps (a)-(c) for the rest of the plurality of spatially offset Raman spectra.

In one embodiment, the determining step comprises the step of determining the tissues that produce the more than one peak in a normalized intensity spectrum as the tissues having a layered structure, where the tissues comprises at least a first type of tissues and s second type of tissues. In one embodiment, the first type of tissues comprise normal tissues, and the second type of tissues comprise cancer tissues.

In another aspect, the present invention relates to a system for surgical margin evaluation of tissues at a surgical site of interest. In one embodiment, the system includes a light source for emitting a coherent light and a probe having a working end, coupled with the light source and for delivering the coherent light to the surgical site to illuminate at least one first spot proximal to the working end, and collecting from the working end Raman scattering light scattered from the surgical site at a plurality of second spots, respectively, in response to illumination by the coherent light, where each second spot is apart from the at least one first spot so as to define a source-detection (S-D) offset distance between the at least one first spot illuminated with the light and the second spot from which the Raman scattering light is collected. The system may include in-line bandpass and longpass filters placed on the working end of the probe.

In one embodiment, the S-D offset distance is smaller than 50 mm. The at least one first spot comprises a plurality of first spots, and wherein the number of the plurality of first spots is smaller than the number of the plurality of second spots.

The light source comprises a laser. In one embodiment, the probe comprises at least one first fiber positioned over the at least one first spot of the surgical site for delivering the light thereto, and at least one second fiber positioned over the surgical site and translationally movable from one to another of the plurality of second spots for collecting the Raman scattering light therefrom. In another embodiment, the probe comprises at least one first fiber positioned over the at least one first spot of the surgical site for delivering the light thereto, and a plurality of second fibers spatially arranged surrounding the at least one first fiber, each second fiber adapted for collecting the Raman scattering light from a corresponding second spot. In yet another embodiment, the probe comprises a fiber array having at least one first fiber, and a plurality of second fibers, where the at least one first fiber and the plurality of second fibers spatially arranged in a row or in a matrix form, the at least one first fiber is adapted for delivering the light to the at least one first spot of the surgical site, and the plurality of second fibers is adapted for collecting the Raman scattering light from the plurality of second spots of the surgical site. In one embodiment, the probe comprises a fiber array having at least one first fiber, and a plurality of second fibers spatially arranged in a radial ring form originated from the at least one first fiber, where the at least one first fiber is adapted for delivering the light to the at least one first spot of the surgical site, and the plurality of second fibers is adapted for collecting the Raman scattering light from the plurality of second spots of the surgical site.

The system also includes a detector coupled with the probe for obtaining the plurality of spatially offset Raman spectra from the collected Raman scattering light, where each spatially offset Raman spectrum is corresponding to a respective second spot of the surgical site, and associated with a depth of the tissues at which the Raman light is scattered. The detector comprises at least one of a spectrograph and a CCD camera.

The system further includes a processor coupled with the detector and programmed to identify tissue signatures from the plurality of spatially offset Raman spectra; and determine surgical margins of the surgical site from the identified tissue signatures. In one embodiment, the processor is programmed to perform the step of comparing each of the Raman spectrum acquired from the at least one first spot and the plurality of spatially offset Raman spectra with a standard Raman spectrum of tumor tissues so as to determine a tumor signature of the corresponding Raman spectrum using a chemometric method such as spare-multinomial linear regression. In another embodiment, the processor is programmed to perform the steps of (a) identifying spectral peaks of one of the plurality of spatially offset Raman spectra at a corresponding S-D offset distance; (b) calculating the tumor signature, $\{T(i)\}$, for each identified peak of the one of the plurality of spatially offset Raman spectra at the corresponding S-D offset distance:

$$T(i)=[I_{SD}(i)-I_N(i)]/[I_{tumor}(i)-I_N(i)),$$

where $i=1, 2, \ldots, N$, N being the number of the spectral peaks, $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively; (c) averaging the tumor signature $\{T(i)\}$ for the N spectral peaks of the one of the plurality of spatially offset Raman spectra to obtain an overall relative tumor contribution in the one of the plurality of spatially offset Raman spectra; and (d) repeating steps (a)-(c) for the rest of the plurality of spatially offset Raman spectra. In yet another embodiment, the processor is programmed to perform the step of determining the tissues that produce the more than one peak in a normalized intensity spectrum as the tissues having a layered structure. The tissues comprises at least a first type of tissues and s second type of tissues, where the first type of tissues comprise normal tissues, and the second type of tissues comprise cancer tissues.

In yet another aspect, the present invention relates to a method for discriminating soft biological tissues. In one embodiment, the method includes the steps of illuminating soft biological tissues at least one first spot with light; collecting Raman scattering light scattered from the soft biological tissues at least second spot in response to illumination by the light, wherein the at least second spot is away from the at least one first spot so as to define a source-detection (S-D) offset distance therebetween; obtaining a spatially offset Raman spectrum from the collected light, wherein the spatially offset Raman spectrum is associated with a depth of the soft biological tissues at which the Raman light is scattered; identifying tissue signatures from the spatially offset Raman spectrum; and determining whether the soft biological tissues have a layered structure from the tissue signatures from the spectrum.

In one embodiment, the at least one first spot comprises a plurality of first spots, the at least second spot comprises a plurality of second spots, and the total number of the plurality of first spots is smaller than the total number of the plurality of second spots.

In one embodiment, the illuminating step is performed by delivering the light generated from a laser to the at least one first spot of the soft biological tissues through one or more source fibers. The collecting step comprises is performed by collecting the Raman scattering light from the at least second spot of the soft biological tissues through one or more collection fibers.

In one embodiment, the identifying step comprises the step of comparing the spatially offset Raman spectrum with a standard Raman spectrum of tumor tissues so as to determine a tumor signature of the spatially offset Raman spectrum, using a statistical chemometrics method including a spare-multinomial linear regression. In yet another embodiment, the identifying step comprises the steps of identifying spectral peaks of the spatially offset Raman spectrum; calculating the tumor signature, $\{T(i)\}$, for each identified peak of the spatially offset Raman spectrum:

$$T(i)=[I_{SD}(i)-I_N(i)]/[I_{tumor}(i)-I_N(i)),$$

where $i=1, 2, \ldots, N$, N being the number of the spectral peaks, and $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively; and averaging the tumor signature $\{T(i)\}$ for the N spectral peaks of the spatially offset Raman spectrum to obtain an overall relative tumor contribution in the spatially offset Raman spectrum.

In one embodiment, the determining step comprises the step of determining the tissues that produce the more than one peak in a normalized intensity spectrum as the tissues having a layered structure. The tissues has a layered structure comprise at least a layer of a first type of tissues and a layer of a second type of tissues, where the first type of tissues comprise normal tissues, and the second type of tissues comprise cancer tissues.

In a further aspect, the present invention relates to a system for discriminating layered soft biological tissues. In one embodiment, the system has means for illuminating soft biological tissues at least one first spot with light; means for collecting Raman scattering light scattered from the soft biological tissues at least second spot in response to illumination by the light, wherein the at least second spot is away from the at least one first spot so as to define a source-detection (S-D) offset distance therebetween; means for obtaining a spatially offset Raman spectrum from the collected light, wherein the spatially offset Raman spectrum is associated with a depth of the soft biological tissues at which the Raman light is scattered; and means for identifying tissue signatures from the spatially offset Raman spectrum, and determining whether the soft biological tissues have a layered structure from the tissue signatures from the spectrum.

In one embodiment, the illuminating means comprises a laser for generating a coherent light and a plurality of source fibers for delivering the generated coherent light to the at least one first spot of the soft biological tissues. The collecting means comprises a plurality of collection fibers positioned over the at least second spot of the soft biological tissues for collecting Raman scattering light therefrom. The plurality of source fibers and the plurality of collection fibers are arranged in the form of one-dimensional array or a matrix.

In one embodiment, the system may further includes a translating stage coupled with the plurality of collection fibers for translationally moving the plurality of collection fibers to a desired location at the soft biological tissues for collecting the Raman scattering light therefrom.

In one embodiment, the obtaining means comprises at least one of a spectrograph and a CCD camera.

In one embodiment, the identifying and determining means comprises a processor that is programmed to perform the step of comparing the spatially offset Raman spectrum with a standard Raman spectrum of tumor tissues so as to determine a tumor signature of the spatially offset Raman spectrum using a statistical chemometrics method including a spare-multinomial linear regression. In another embodiment, the processor is programmed to further perform the steps of identifying spectral peaks of the spatially offset Raman spectrum; calculating the tumor signature, $\{T(i)\}$, for each identified peak of the spatially offset Raman spectrum:

$$T(i)=[I_{SD}(i)-I_N(i)]/[I_{tumor}(i)-I_N(i)],$$

where $i=1, 2, \ldots, N$, N being the number of the spectral peaks, and $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively; and averaging the tumor signature $\{T(i)\}$ for the N spectral peaks of the spatially offset Raman spectrum to obtain an overall relative tumor contribution in the spatially offset Raman spectrum.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
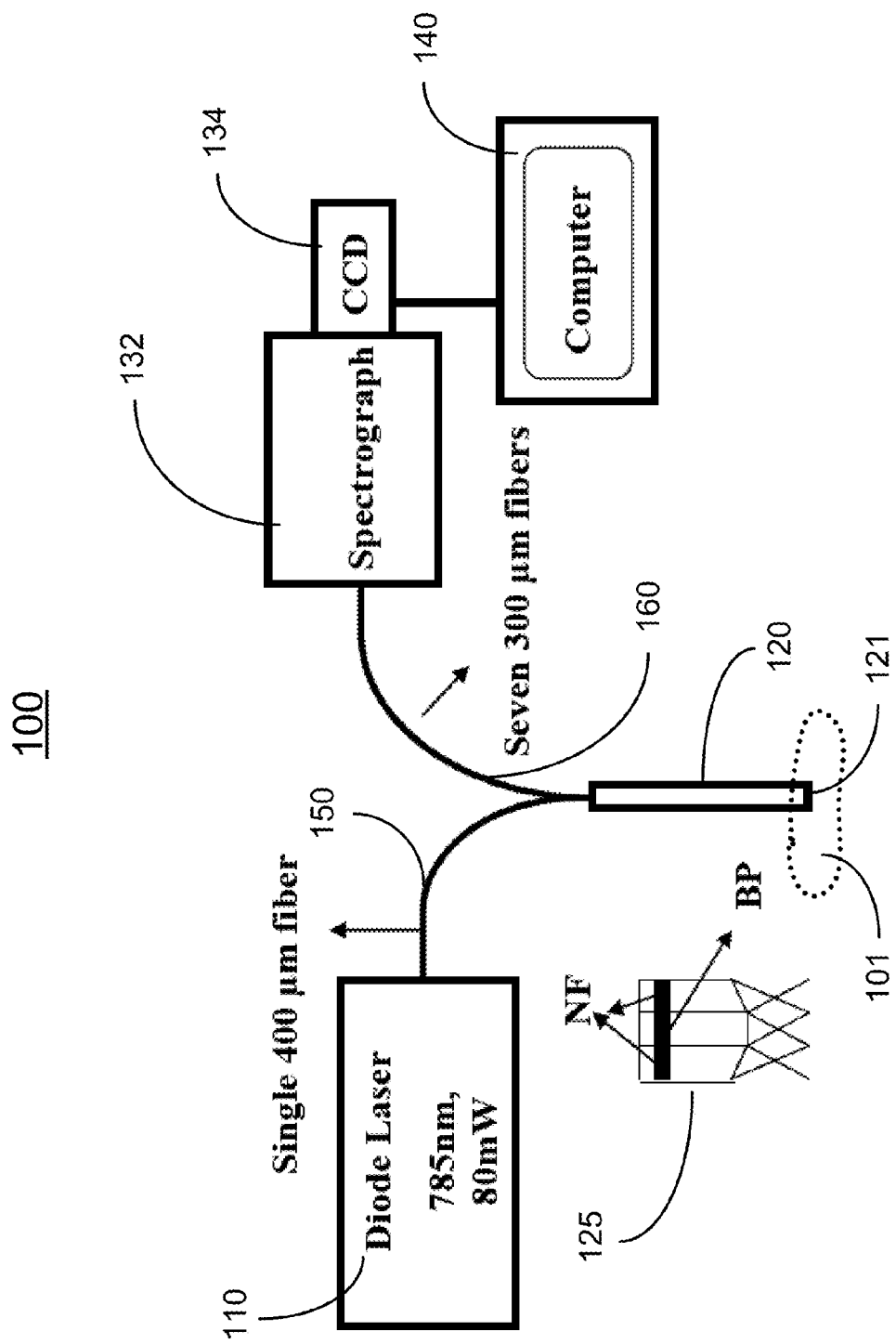
FIG. 1 shows schematically an experimental setup for acquiring SORS spectra according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprising," "including," "having," "containing," "involving," and the like are to be understood to be open-ended, i.e., to mean including but not limited to.

OVERVIEW OF THE INVENTION

Raman spectroscopy is based on inelastic scattering, which occurs when an incident photon causes a scattering molecule to enter a virtual excited state, and then return to a ground state either higher or lower than the original through the emission of another photon. Raman scattering involves transitions between vibrational energy levels. A Raman spectrum includes a series of peaks, which represent the different vibrational modes of the scattering molecules. These peaks are spectrally narrow and molecular-specific, such that the observed peaks may be associated with specific bonds in specific molecules. Many biological molecules have distinguishable spectra, so that one can determine the gross biochemical composition of a tissue from its Raman spectrum. One particularly relevant biochemical change for cancer cells is an increase in the nucleic acid content concomitant with increased proliferation and genetic instability. This change, among others like changes in glycogen and collagen, can be detected with Raman spectroscopy.

Raman spectroscopy has been widely used for cancer diagnosis, but conventional forms provide limited depth information. Spatially offset Raman spectroscopy (SORS) can solve the depth issue, but it has only been used to detect hard tissues like bone. In SORS, larger offsets are more likely to detect photons that have traveled deeper into tissue via multiple scattering compared with smaller separations, which detect superficial photons that have only undergone minimal scattering events. Matousek et al. demonstrated SORS of diffusely scattering media using a two-layer chemical phantom [4]. The same group demonstrated the biological application of this technique in detecting the strong Raman signature of bone through several mm of soft tissue [5], which has been further advanced by Schulmerich et al. [6]. Stone et al. demonstrated the use of this technique to detect the Raman spectral features of hydroxyapatite crystals (found in breast calcifications) through overlying lean chicken breast tissue [7]. Most recently, Macleod et al. used SORS to predict the thicknesses of soft tissue layers over bone [8]. Thus, the application of SORS has been limited to detecting very strong scatterers with unique spectral features, either chemicals or hard tissue, under a layer of generic soft tissue. No work has yet been reported in applying SORS to discriminating multiple layers of soft tissue or for detecting cancer through overlying layers of normal tissue that would normally block the tumor spectral signatures.

In this disclosure, the feasibility of using SORS to discriminate two types of soft tissue and for surgical margin evaluation of tissues at a surgical site is exhibited. Measurements are taken with individual source and detector fibers at a number of spatial offsets from samples having various thicknesses of normal human breast tissues overlying breast tumors. Results show that SORS can detect tumors beneath normal tissue, marking the first application of SORS for discriminating two types of soft tissues.

One aspect of the present invention provides a system for surgical margin evaluation of tissues at a surgical site during breast conserving therapy (BCT). This process involves a partial mastectomy for the removal of the primary breast lesion, usually followed by directed radiotherapy. BCT is an option for most women diagnosed with early-stage breast cancer, and provides superior cosmetic results and equivalent long-term survival when compared with total mastectomy [9]. To be successful, BCT must provide negative margins, meaning there is no presence of tumor in the removed tissue within 1-2 mm (depending on hospital) of the surgical margin.

As shown in FIG. 1, the system 100 includes a light source 110 for emitting a coherent light and a probe 120 having a working end 121, coupled with the light source 110. The probe 120 is adapted for delivering the coherent light to the surgical site 101 to illuminate at least one first spot (not shown) proximal to the working end 121, and collecting from the working end 121 Raman scattering light scattered from the surgical site 101 at a plurality of second spots (not shown), respectively, in response to illumination by the coherent light. Each second spot is apart from the at least one first spot so as to define a source-detection (S-D) offset distance between the at least one first spot illuminated with the light and the second spot from which the Raman scattering light is collected. Generally, the S-D offset distance is smaller than 50 mm. The at least one first spot may have a plurality of first spots, and the number of the plurality of first spots is smaller than the number of the plurality of second spots. The system may include in-line bandpass and longpass filters 125 placed on the working end 121 of the probe 120 for rejecting signals generated in the probe (fibers). In the example, the light source is a diode laser having a wavelength at 785 nm with about 80 mW output. Other types of lasers or coherent light sources can also be utilized to practice the present invention.

The probe 120 includes at least one first fiber 150 coupled to the laser 110 for delivering the light to the at least one first spot of the surgical site 101, and at least one second fiber 160 for collecting the Raman scattering light therefrom. The at least one second fiber 160 is coupled to the detector. The detector includes a spectrograph 132 and a CCD camera 134 adapted for obtaining the plurality of spatially offset Raman spectra from the collected Raman scattering light. Each spatially offset Raman spectrum is corresponding to a respective second spot of the surgical site, and associated with a depth of the tissues at which the Raman light is scattered.

The system 100 further includes a processor (computer) 140 coupled with the spectrograph 132 and/or the CCD camera 134 and programmed to identify tissue signatures from the plurality of spatially offset Raman spectra and determine surgical margins of the surgical site from the identified tissue signatures. Once the Raman spectra is received from the spectrograph 132 and/or the CCD camera 134 by the computer 140, it compares each of the Raman spectrum acquired from the at least one first spot and the plurality of spatially offset Raman spectra with a standard Raman spectrum of tumor tissues to determine a tumor signature of the corresponding Raman spectrum. In one embodiment, the comparing step is performed with a statistical chemometrics method including a spare-multinomial linear regression. The standard Raman spectra of tumor tissues and normal tissues are pre-acquired and stored in the computer 140 for use.

Specifically, the computer 140 performs the steps of (a) identifying spectral peaks of one of the plurality of spatially offset Raman spectra at a corresponding S-D offset distance; (b) calculating the tumor signature, $\{T(i)\}$, for each identified peak of the one of the plurality of spatially offset Raman spectra at the corresponding S-D offset distance:

$$T(i)=[I_{SD}(i)-I_N(i)]/[I_{tumor}(i)-I_N(i)],$$

where $i=1, 2, \ldots, N$, N being the number of the spectral peaks, $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively; (c) averaging the tumor signature $\{T(i)\}$ for the N spectral peaks of the one of the plurality of spatially offset Raman spectra to obtain an overall relative tumor contribution in the one of the plurality of spatially offset Raman spectra; and (d) repeating steps (a)-(c) for the rest of the plurality of spatially offset Raman spectra.

Figure 2:
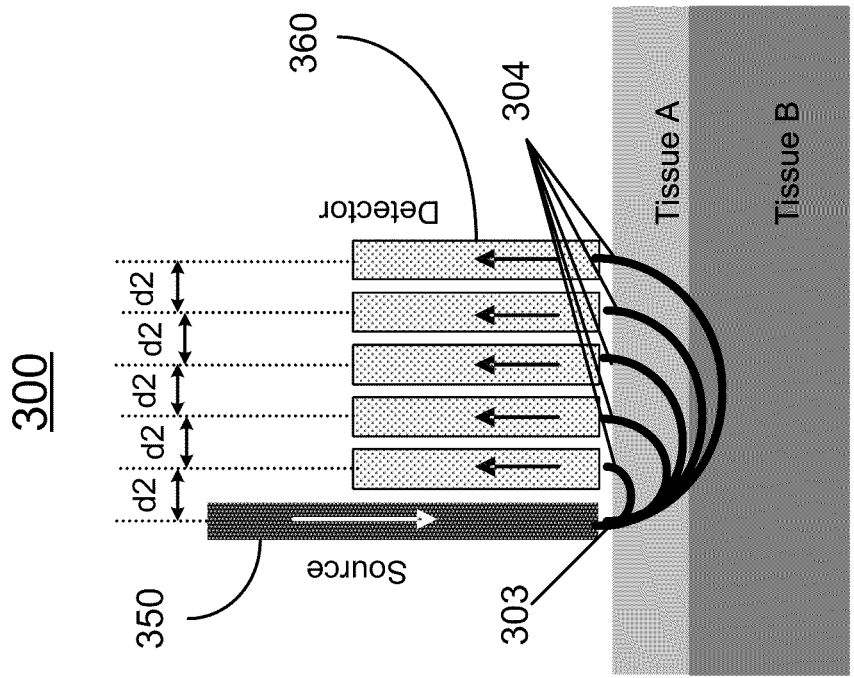
FIG. 2 shows schematically a partially experimental setup for acquiring SORS spectra according to one embodiment of the present invention.
Figure 12:
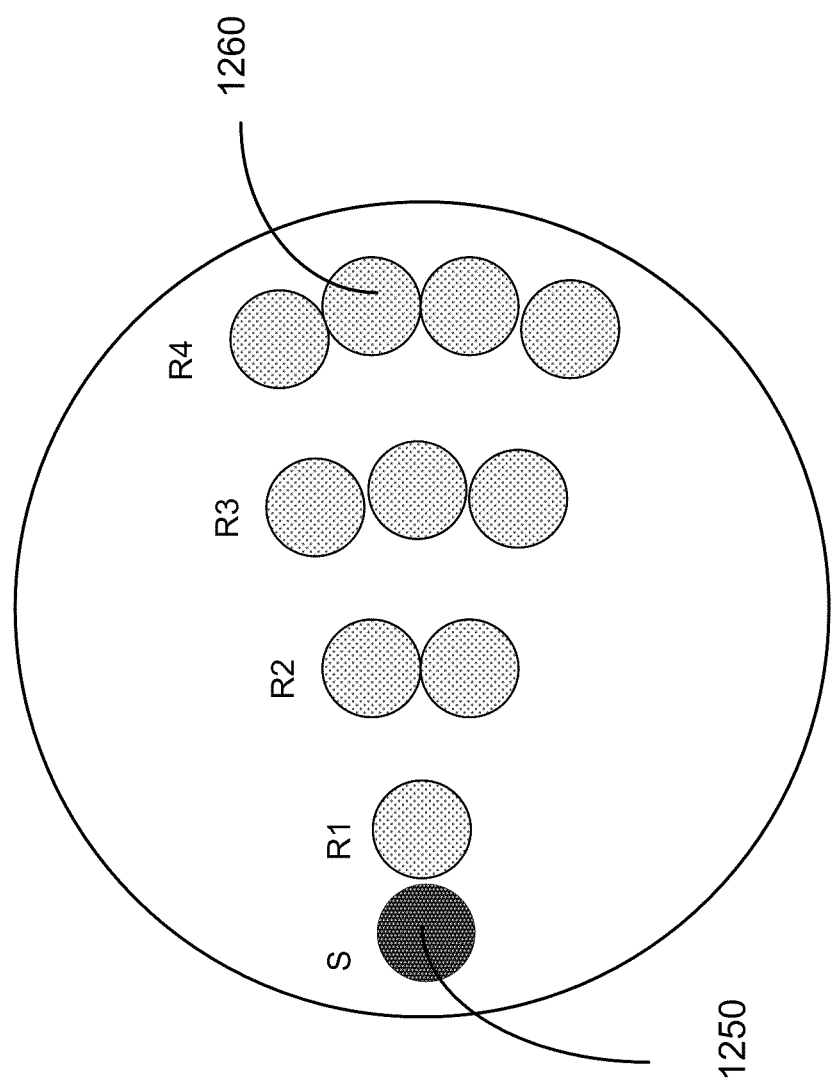
FIG. 12 shows a schematic of tip of SORS probe according to one embodiment of the present invention. S—source fiber, all other circles—collection fibers. Each ring of collection fibers is separated by 1 mm (center to center) from the previous ring, with 0.5 mm between the centers of the source fiber and the first detector ring (R1).

The probe may have various configurations. For example, as shown in FIG. 2, the probe includes a source fiber 250 positioned over a first spot 203 and a collection fiber 160 positioned over a second spot. The first and second spots define an S-D offset distance, d1, therebetween. In the example, the collection fiber 260 is translationally movable along a straight line 290 so that it is capable of collecting the Raman scattering light at various S-D offsets. FIG. 12 shows another embodiment of the probe that has a source fiber 1250 and a plurality of collection fibers 1260 spatially arranged in a radial ring form originated from the source fiber 1250.

Figure 3:
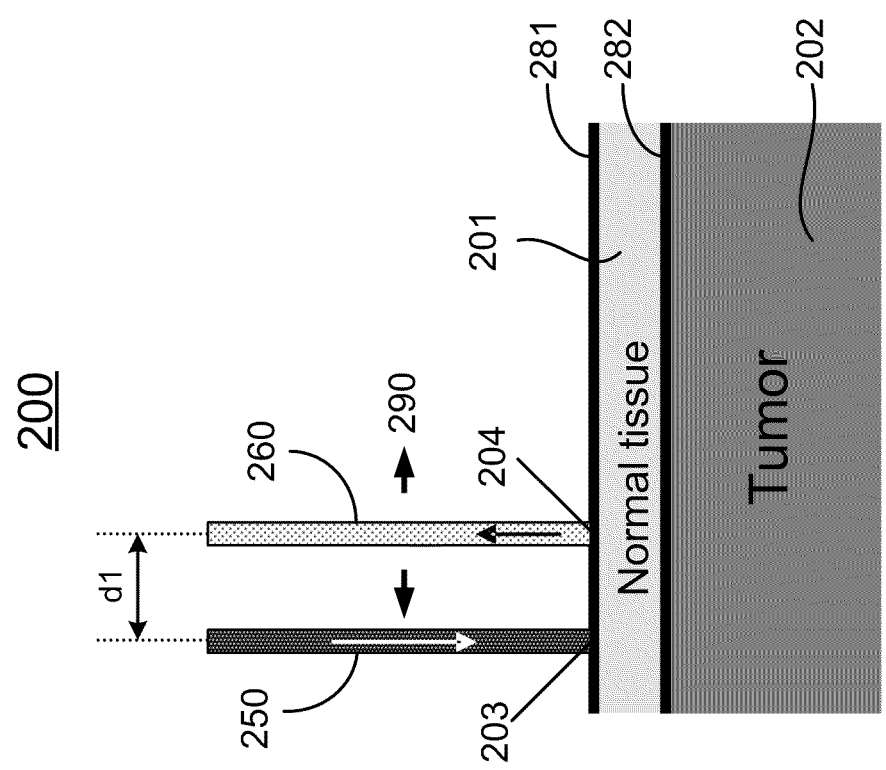
FIG. 3 shows schematically a partially experimental setup for acquiring SORS spectra according to another embodiment of the present invention.

As shown in FIG. 3, the probe includes a source fiber 350 positioned over a first spot 303 and four collection fibers 360 positioned over four second spots 304. The source fiber 350 and the four collection fibers 360 are aligned in a one-dimensional array at a distance, d2. The probe is also capable of collecting the Raman scattering light at various S-D offsets, i.e., each collection fiber 360 collects the Raman scattering light at a corresponding second spot 304.

Figure 4:
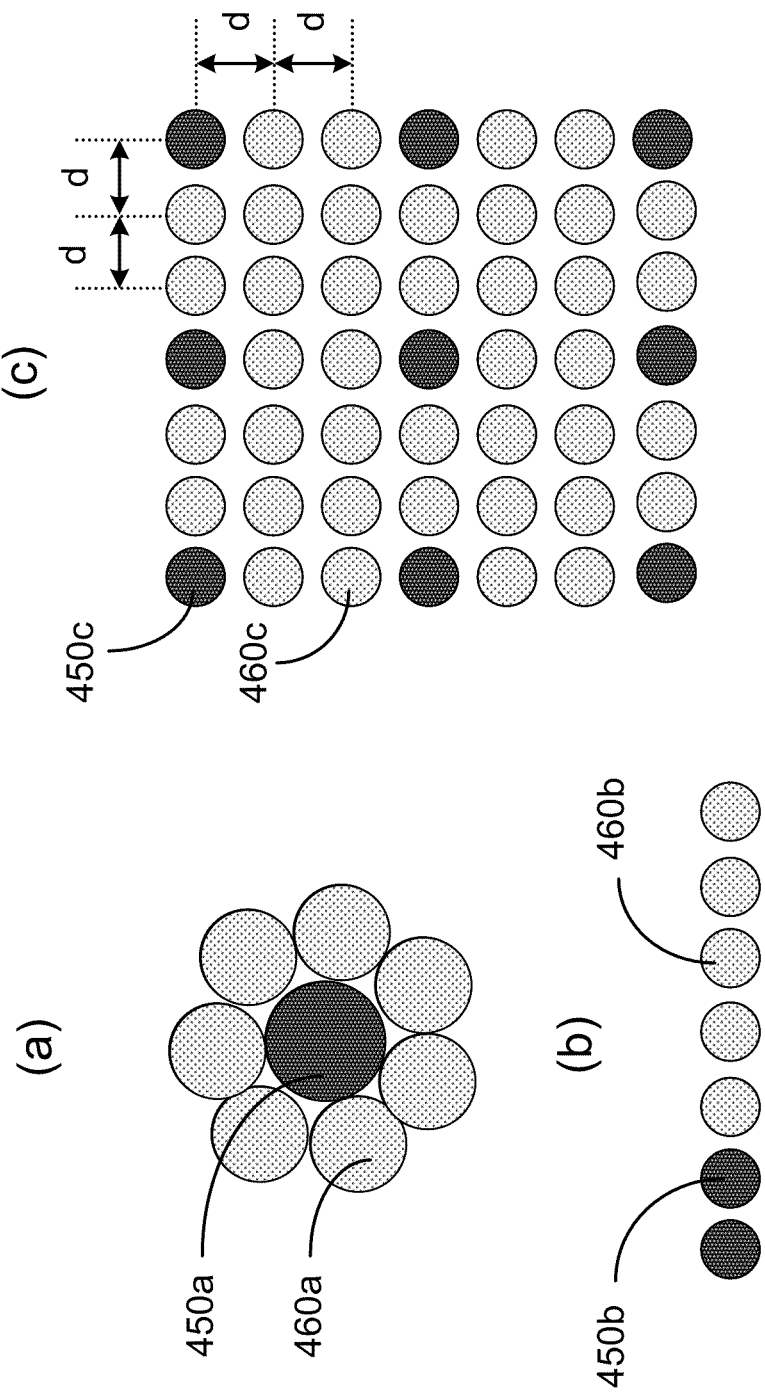
FIG. 4 shows schematically three arrangements (a)-(c) of the source fibers and the collection fibers according to embodiments of the present invention.

FIG. 4 shows various arrangements of the source fibers 350a/350b/350c and the collection fibers 360a/360b/360c of the probe.

In all these arrangements of the probe, the source fibers are adapted for delivering the light to the at least one first spot of the surgical site, and the collection fibers are adapted for collecting the Raman scattering light from one or more second spots that are apart from the at least one first spot, such that each spatially offset Raman spectrum is corresponding to a respective second spot of the surgical site, and associated with a depth of the tissues at which the Raman light is scattered.

Another aspect of the present invention provides a method for surgical margin evaluation of tissues at a surgical site of interest. The method in one embodiment includes the steps of acquiring a plurality of spatially offset Raman spectra from the surgical site, identifying tissue signatures from the plurality of spatially offset Raman spectra, and determining surgical margins of the surgical site from the identified tissue signatures.

The acquiring step comprises the following steps: at first, at least one first spot of the surgical site is illuminated with light. Then, Raman scattering light from the surgical site at a plurality of second spots is respectively collected. Each second spot is apart from the at least one first spot so as to define a source-detection (S-D) offset distance between the at least one first spot illuminated with the light and the second spot from which the Raman scattering light is collected. Next, the plurality of spatially offset Raman spectra is obtained by a spectrograph and/or a CCD camera from the collected Raman scattering light. Each spatially offset Raman spectrum is corresponding to a respective second spot of the surgical site, and associated with a depth of the tissues at which the Raman light is scattered.

The acquiring step is performed with a probe having a working end and in-line filters placed on the working end.

The method further comprises the step of acquiring a Raman spectrum from the at least one first spot illuminated with the light.

In one embodiment, the identifying step comprises the step of comparing each of the Raman spectrum acquired from the at least one first spot and the plurality of spatially offset Raman spectra with a standard Raman spectrum of tumor tissues so as to determine a tumor signature of the corresponding Raman spectrum. The identifying step is performed with a chemometric or other statistical techniques to determine the surgical margin status and/or size of the negative margin, wherein the statistical chemometrics method including a spare-multinomial linear regression, and/or the classical least squares (CLS) method. Furthermore, the identifying step comprises the steps of (a) identifying spectral peaks of one of the plurality of spatially offset Raman spectra at a corresponding S-D offset distance, (b) calculating the tumor signature, $\{T(i)\}$, for each identified peak of the one of the plurality of spatially offset Raman spectra at the corresponding S-D offset distance $$T(i)=[I_{SD}(i)-I_N(i)]/[I_{tumor}(i)-I_N(i)],$$

where $i=1, 2, \ldots, N$, N being the number of the spectral peaks, $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively, (c) averaging the tumor signature $\{T(i)\}$ for the N spectral peaks of the one of the plurality of spatially offset Raman spectra to obtain an overall relative tumor contribution in the one of the plurality of spatially offset Raman spectra, and (d) repeating steps (a)-(c) for the rest of the plurality of spatially offset Raman spectra.

In one embodiment, the determining step comprises the step of determining the tissues that produce the more than one peak in a normalized intensity spectrum as the tissues having a layered structure, where the tissues comprises a layer of normal tissue and a layer of cancer tissue.

Additionally, the invention discloses an apparatus that uses spatially offset Raman spectroscopy (SORS) to obtain depth-sensitive information from the margins of tumors to determine whether those margins are positive or negative, i.e., whether a sufficient safety zone exists around the tumor to minimize the risk of local recurrence. The novelty of this technique is apparent by the lack of any published demonstrations of this technology for tumor margin assessment. To date, SORS has only been shown to be capable of detecting bone and calcification signatures beneath soft tissue, but not for detecting tumor signatures under normal soft tissue, or therapeutic guidance in general.

The invention can find many applications. One application of this invention, as disclosed here, is breast conserving surgery, which currently relies on standard histopathology to examine surgical margins, forcing a large percentage of women to later undergo a second tumor removal surgery when it is discovered that the surgeon created an insufficient margin around the tumor. The surgeon also has intra-operative techniques available to him to examine margins, but these all have significant shortcomings in terms of accuracy, time, and/or cost that this invention can overcome.

At this time, the technology has been shown to successfully detect breast tumor signatures beneath 2 mm of normal breast tissue in small pilot studies using frozen breast tissue samples and in the clinic.

In accordance with the purposes of this invention, as embodied and broadly described herein, this invention, in one aspect, relates to a method for discriminating layered soft biological tissues. In one embodiment, the method comprises the steps of illuminating soft biological tissues at least one first spot; collecting the light scattered from the soft biological tissues at least second spot that is away from the at least one first spot; obtaining a spectrum from the collected light; finding tissue signatures from the spectrum; and determining whether the tissues have a layered structure from the tissue signatures from the spectrum.

The illuminating step comprises the step of illuminating human tissues with light from a laser light source through a plurality of source fibers. The collecting step comprises the steps of collecting the light scattered by a plurality of collection fibers.

The at least second spot is away from the at least one first spot at a non-zero spatially offset distance smaller than 50 mm. In one embodiment, the at least one first spot comprises a plurality of first spots, the at least second spot comprises a plurality of second spots, and the total number of the plurality of first spots is smaller than the total number of the plurality of second spots.

The determining step comprises the step of determining the tissues that produce the more than one peak in a normalized intensity spectrum as the tissues having a layered structure, which can be performed by a medical professional with or without help of a computer.

The tissues having a layered structure comprise a layer of normal tissue and a layer of cancer tissue.

This invention, in another aspect, relates to a system for discriminating layered soft biological tissues. In one embodiment, the system comprises means for illuminating soft biological tissues at least one first spot; means for collecting the light scattered from the soft biological tissues at least second spot that is away from the at least one first spot; means for obtaining a spectrum from the collected light; and means for determining whether the tissues have a layered structure from the tissue signatures from the spectrum.

The means for illuminating soft biological tissues at least one first spot comprises a laser light source and a plurality of source fibers for delivering laser light to illuminate tissues. The means for collecting the light scattered from the soft biological tissues at least second spot that is away from the at least one first spot comprises a plurality of collection fibers.

These and other aspects of the present invention are more specifically described below.

Without intent to limit the scope of the invention, additional exemplary embodiment and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLES OF THE INVENTION

A schematic of the experimental setup for acquiring the SORS spectra is shown in FIG. 2. Layers of normal human breast tissue 201, which include mostly adipose with some fibroglandular tissue, were sealed between two about 100 μm thick quartz coverslips 281 and 282 to prevent dehydration and to minimize the impact of non-biological materials on the results. Normal layer thicknesses of about 0.5 mm, 1 mm and 2 mm were achieved by placing appropriate spacers between the coverslips 281 and 282. These thicknesses were chosen to represent the clinical margin standards and to include a thinner layer as essentially a positive control. These normal layers were placed directly on the top of invasive breast cancer tissue samples 202 obtained fresh-frozen from the Cooperative Human Tissue Network and thawed at room temperature in buffered saline.

SORS measurements were taken with single 200 μm excitation and collection fibers, featuring in-line bandpass and longpass filters, respectively, at their tips (Emvision, Loxahatchee, Fla.). The source fiber 250 was fixed in place and delivered 80 mW of power from a 785 nm diode laser (Innovative Photonics Solutions, Monmouth Junction, N.J.). The collection fiber 260 was able to translate in a straight line 290 to collect the Raman scattering light therefrom and deliver the collected Raman scattering light to the detection elements: for example, an imaging spectrograph (Kaiser Optical Systems, Inc., Ann Arbor, Mich.) and a back illuminated, deep depletion, thermo-electrically cooled charge coupled device (CCD) camera (Andor Technology, Belfast, Northern Ireland). Measurements were taken with spatial offsets from 0.75 mm to 4.75 mm in 0.5 mm intervals. For each offset, two 30 second integrations were acquired and averaged before further analysis. To achieve a smaller offset and as a point of comparison, spectra were also obtained with the same instrumentation but with a more standard fiber optic probe with a central 400 μm delivery fiber and seven surrounding 300 μm collection fibers, all featuring in-line filtering at their tips (Emvision, Loxahatchee, Fla.). All seven fibers were binned after a single 3 second acquisition, and these measurements were considered to be taken with a 0.35 mm source-detector offset. All spectra were calibrated, noise smoothed, and had background fluorescence subtracted as previously described [15]. Normalization was achieved by dividing each processed spectrum by its overall mean intensity.

Figure 5:
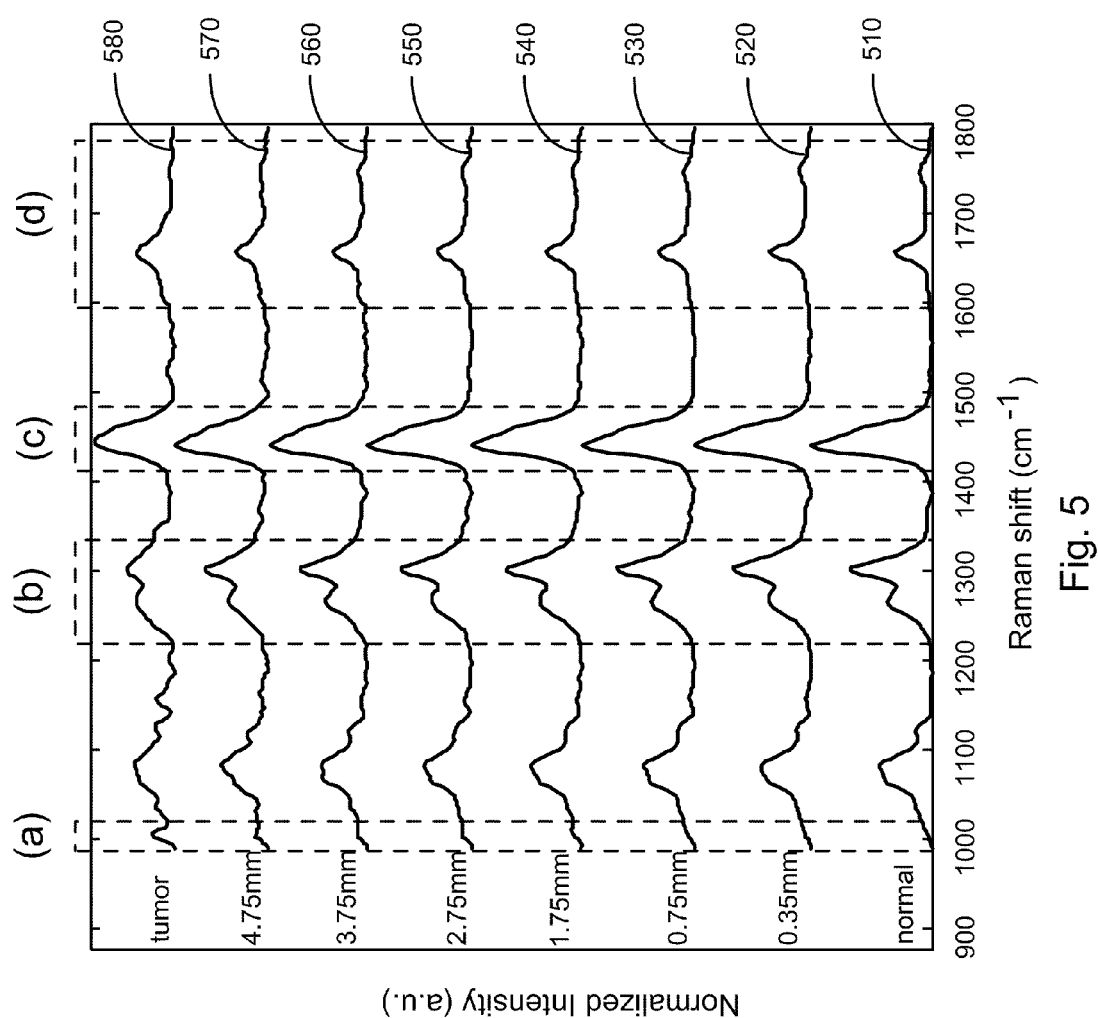
FIG. 5 shows SORS spectra at various S-D offsets from a single experimental run with a 0.5 mm normal layer. Boxes (a)-(d) highlight spectral regions with the most dramatic changes from normal to tumor signatures as the S-D offset increases.
Figure 6:
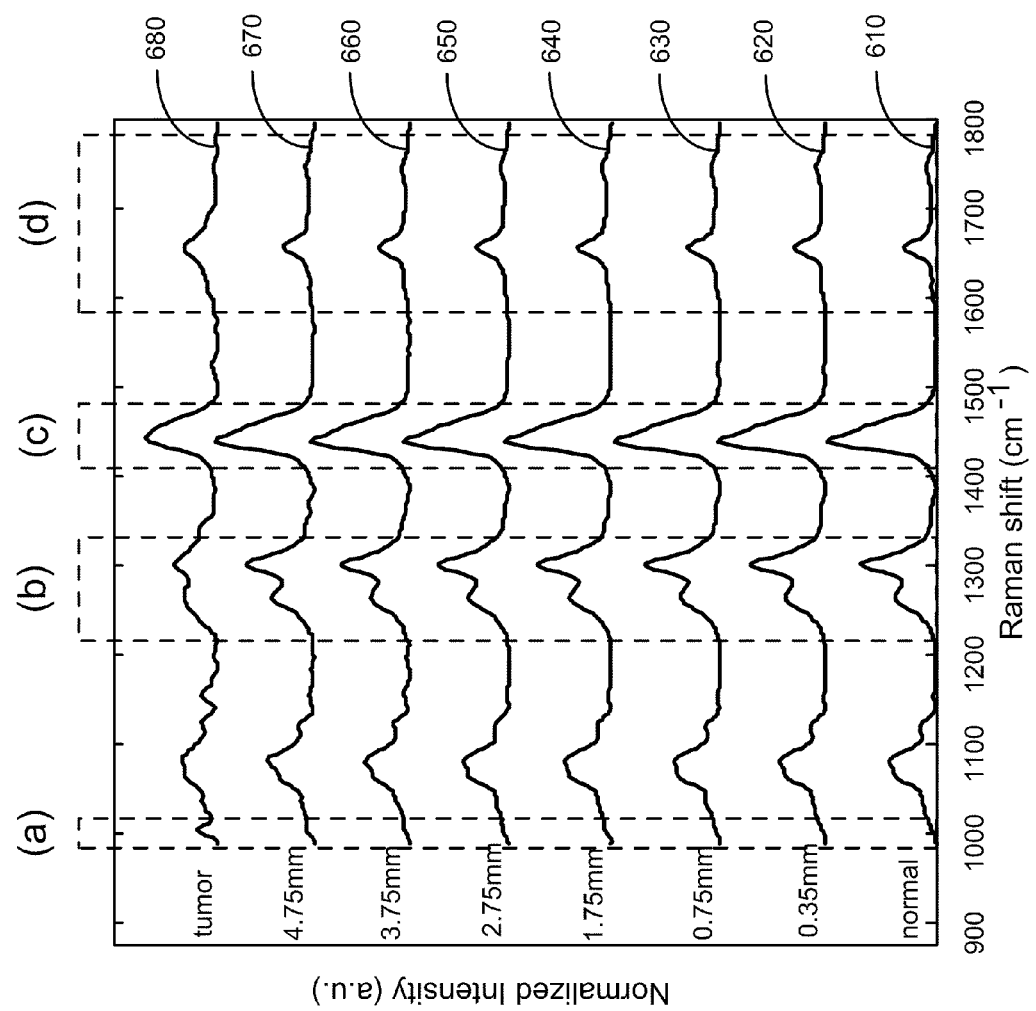
FIG. 6 shows SORS spectra at various S-D offsets from a single experimental run with a 1.0 mm normal layer. Boxes (a)-(d) highlight spectral regions with the most dramatic changes from normal to tumor signatures as the S-D offset increases.
Figure 7:
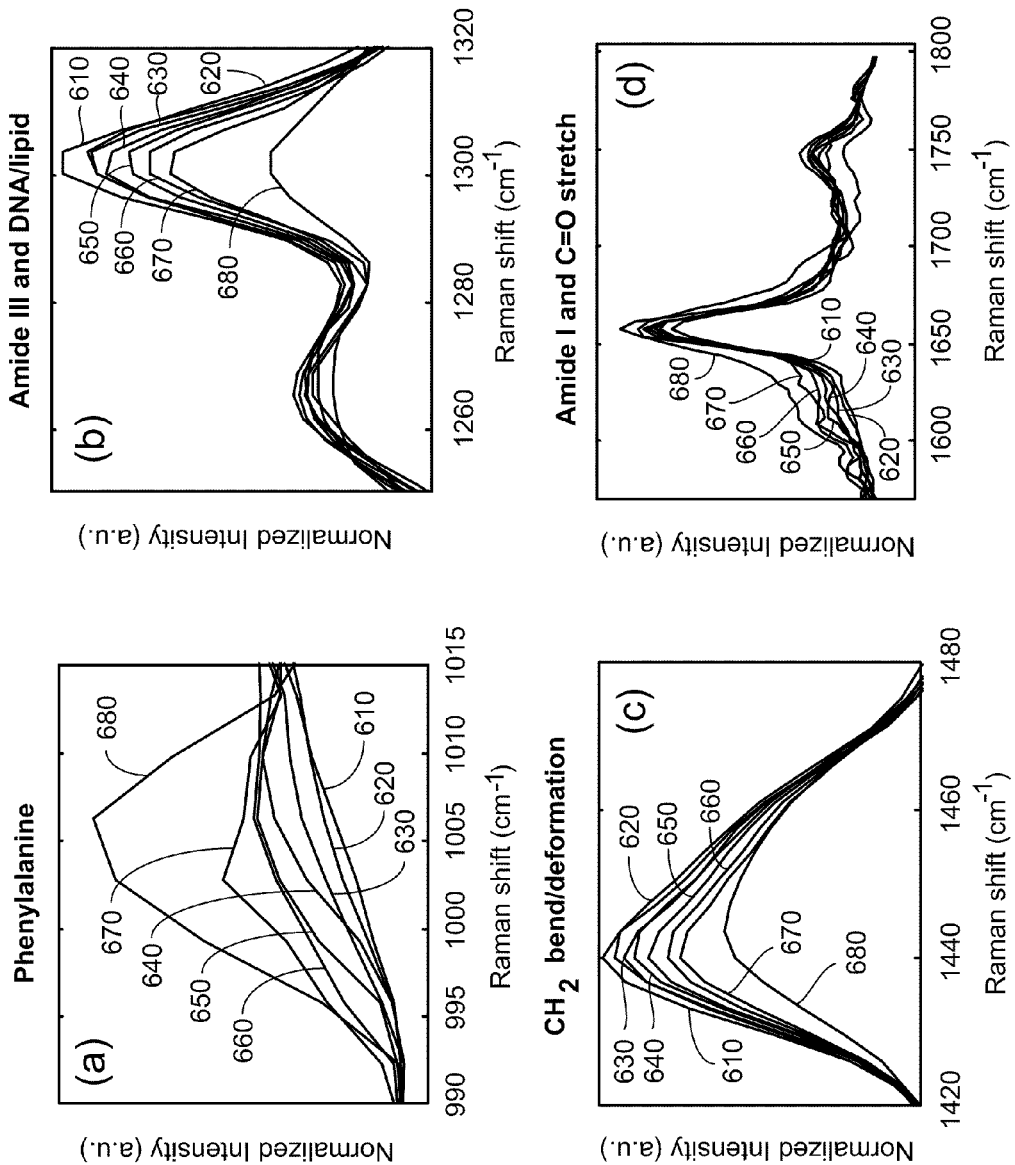
FIG. 7 shows SORS spectra at the spectral regions (a)-(d) as sown in FIG. 6.

FIGS. 5-7 shows SORS spectra 520-570 and 620-670 obtained with a 0.5 mm and 1 mm normal layer over an invasive cancer tissue sample at various S-D offsets, respectively. FIGS. 5-7 also show the mean Raman spectra 510/610 and 580/680 from the individual normal and tumor layers. From a visual inspection, it is clear that as spatial offset increases, the spectra begin to increasingly resemble the tumor spectrum 580/680 compared with the normal spectrum 510/610. Of particular note is that for the standard probe measurement (0.35 mm offset), a normal layer of only 0.5 mm almost completely masks the underlying cancer signature. The dashed-line boxes (a)-(d) in FIGS. 5-7 highlight the spectral regions subject to the most dramatic changes as spatial offset increases. These include the increased presence of the 1006 $cm^{-1}$ peak generally attributed to phenylalanine; a decreasing ratio of the 1303 $cm^{-1}$ to 1270 $cm^{-1}$ peaks, which tends to indicate an increasing protein content; and the increasing width of the amide I peak around 1650 $cm^{-1}$.

Another significant change that is somewhat difficult to appreciate in FIGS. 5-7 is a decrease in the relative intensity of the 1445 cm$^{-1}$ CH$_2$ stretch/deformation peak as spatial offset increases, while other subtle changes include a decrease in the 1743 cm$^{-1}$ carbonyl stretch peak and an increase in the 1150 cm$^{-1}$ carotenoid peak as offset increases.

The results of these examples were quantified by developing a classical least squares (CLS) model via the PLS_toolbox (Eigenvector Research, Wenatchee, Wash.) within a MATLAB (Mathworks, Natick, Mass.) environment. Five Raman measurements from each normal tissue layer only were averaged together, and five measurements from each tumor sample only were averaged; these two means were then used as pure component spectral inputs to create a CLS model. This model was subsequently applied to the spectra collected from each spatial offset, after being averaged across the three experimental runs, to determine the relative contributions of the normal and tumor spectral signatures to the offset spectra. These two relative contributions always sum to 1, and the model was constrained to fitting the data in a non-negative manner.

Figure 8:
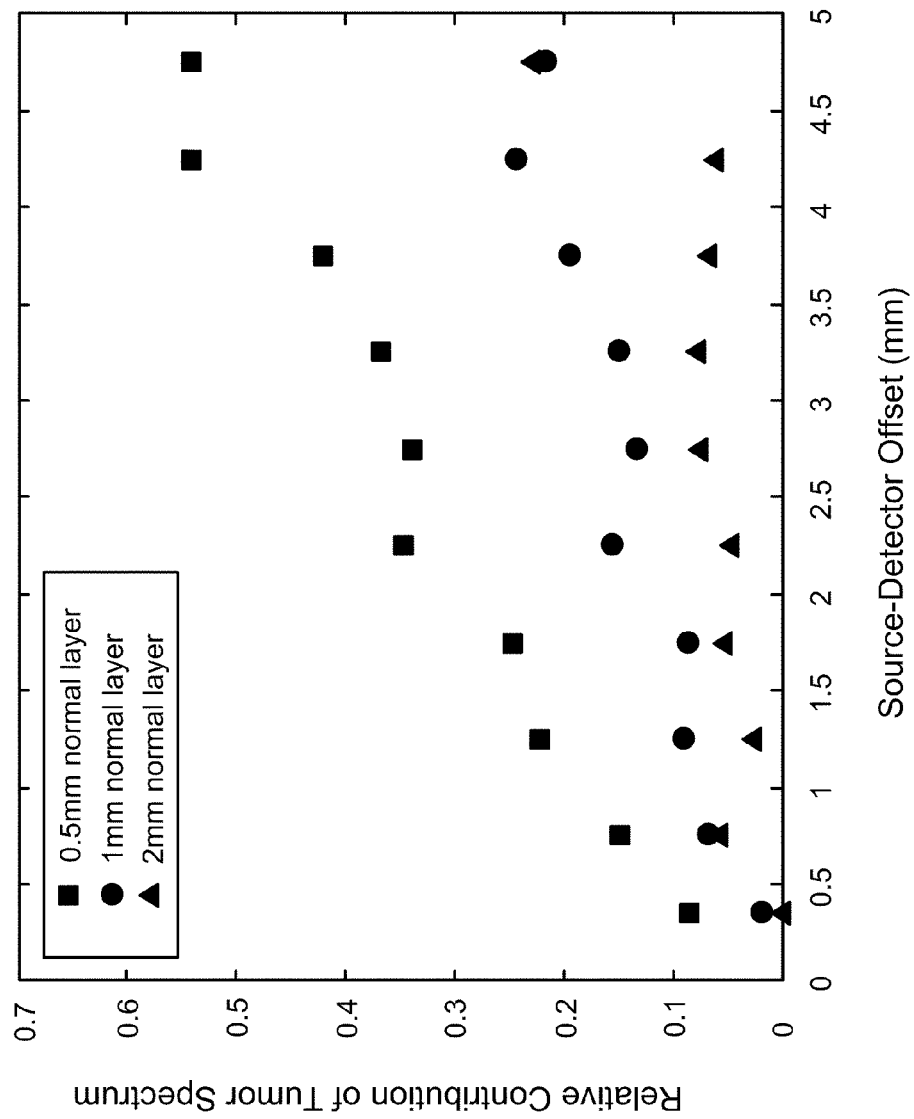
FIG. 8 shows mean relative contributions of the tumor signature to the measured spectra at each S-D offset for the various thicknesses of the normal tissue layer.
Figure 9:
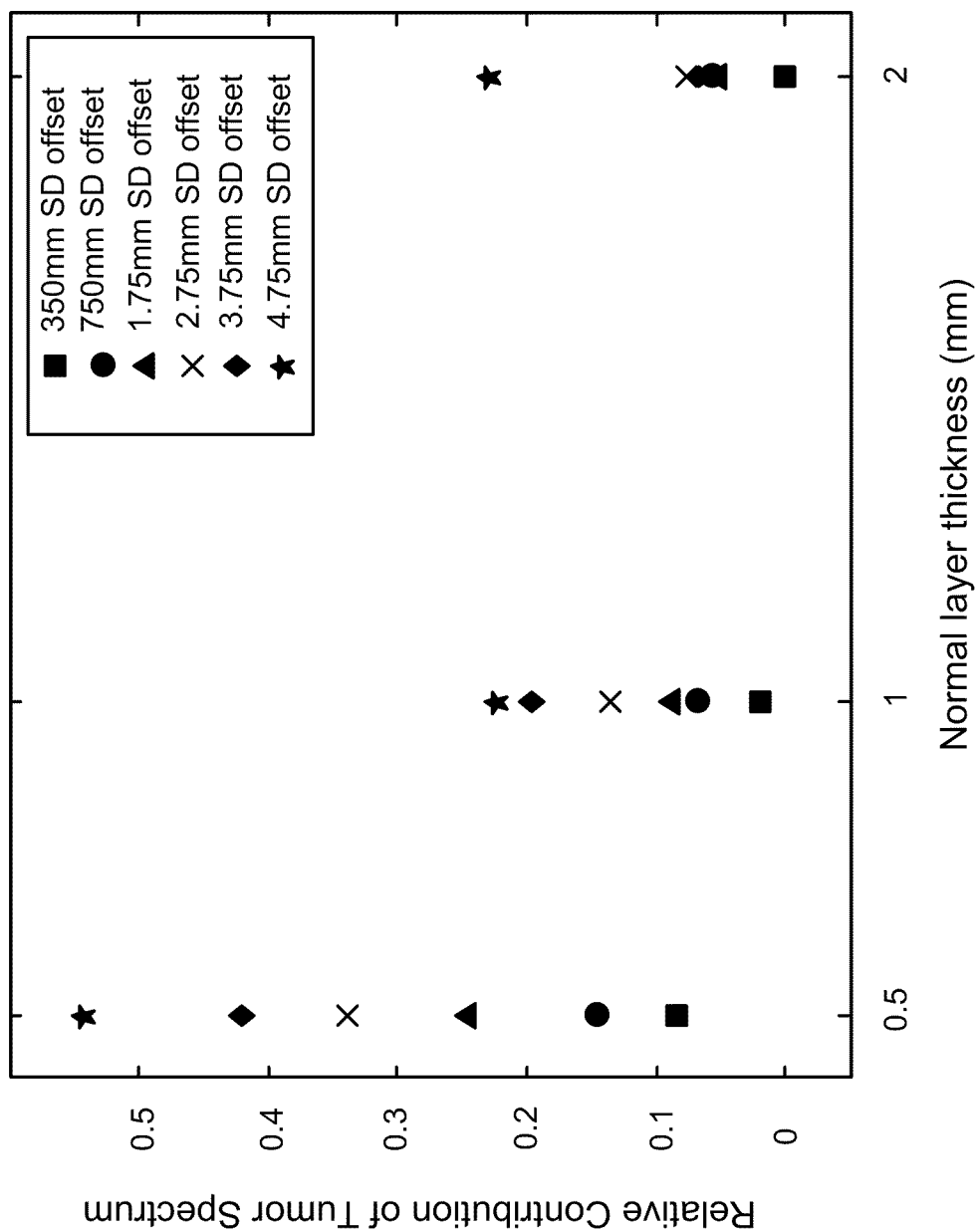
FIG. 9 shows the same data from FIG. 8, but shown as a function of overlying normal layer thickness for the selected S-D offsets.

FIGS. 8 and 9 show the results of the CLS analysis in complementary fashion. Both plot the relative tumor spectrum contributions to the offset spectra on the y axis, but FIG. 8 shows how this metric changes as a function of source-detector offset for the three different normal layer thicknesses, while FIG. 9 displays it as a function of normal layer thickness for a range of spatial offsets. Most generally, both figures quantitatively support the visual evidence from FIGS. 5-7 that SORS can indeed detect Raman spectral contributions from breast tumors beneath the relevant depths of normal tissue that standard configurations (0.35 mm offset) cannot. From FIG. 8, this effect follows a quadratic-shaped or logarithmic-shaped response as spatial offset increases, and it seems to indicate that for this tissue system, S-D offsets of more than about 4 mm do not provide any additional useful information. An interesting effect is shown most explicitly in FIG. 9 by the tighter bunching of data points along the y axis as one moves along the x axis. This observation shows that as the normal layer thickness increases, there is a diminishing increase in relative contribution from the bottom layer as S-D offset increases. FIG. 9 also shows the dramatic effect that moving a detection fiber from next to the delivery fiber to just 1.5 mm further away has on the ability to detect Raman photons from deeper tissue layers for this application. From FIG. 8, it is shown that at a given source-detector separation, what relative contribution of tumor spectrum to overall spectrum signifies a given depth of superficial normal tissue, while FIG. 9 show that at a given source-detector separation, use the relative contribution of tumor spectrum to determine exact thickness of overlying normal tissue layer.

The findings of these examples have some similarities to and differences from previous SORS studies. The shapes of the responses to changes in spatial offset and top layer thickness in FIGS. 8 and 9, respectively, match up well with similar plots in earlier studies [4, 8]. Unlike earlier reports, these trends were observed with two layers of soft tissue whose Raman spectra differ only by relative ratios and widths of peaks, without the presence of strong, unique bands in the bottom layer. This may limit the use of some analytical techniques used in other SORS studies. A simple, two component CLS model worked well for the lab measurements, although a more complex model or an entirely different method of analysis may prove necessary for clinical applications. Further, statistical techniques, such as sparse multinomial logistic regression, may be included, which simply look for the presence of breast cancer signatures within the first 2 mm of the excised tissue surface.

Figure 10:
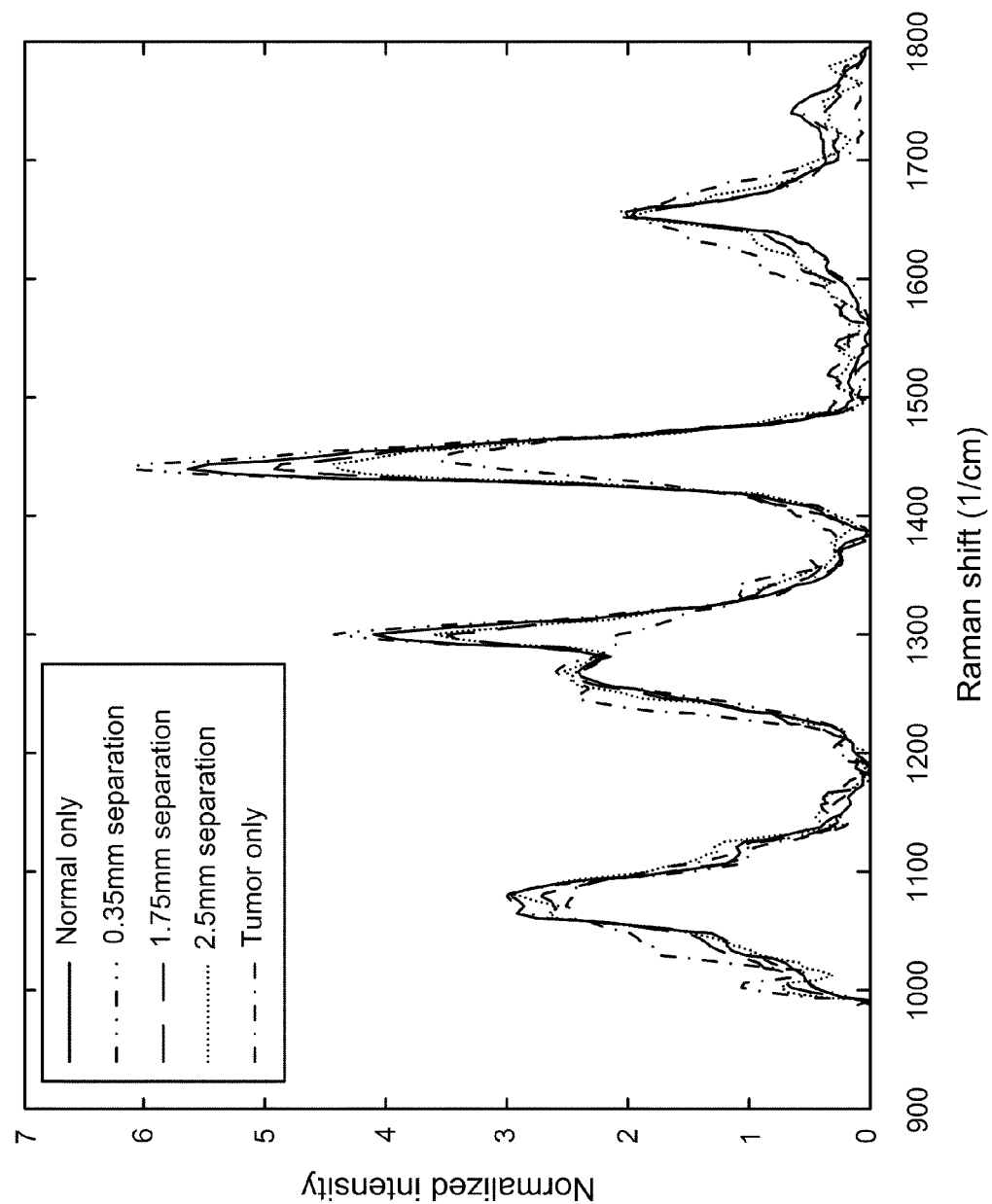
FIG. 10 shows SORS spectra at various S-D offsets for fat over a muscle phantom.

FIG. 10 shows SORS spectra at various S-D offsets for fat over a muscle phantom, which indicate the SORS spectra can be utilized for surgical margin evaluation during breast conserving therapy and discriminating two layers of soft tissues.

SORS Spectra for Breast Tumor Surgical Margin Evaluation

Figure 11:
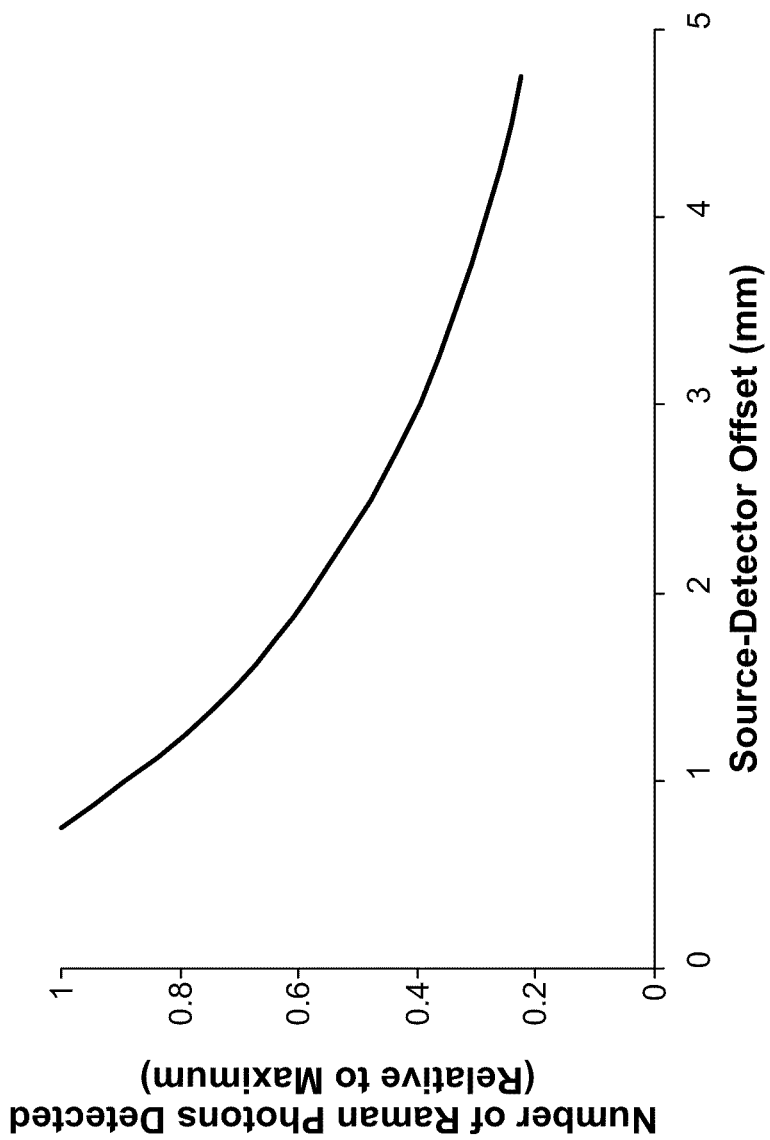
FIG. 11 shows simulation results for total number of Raman photons detected as a function of S-D offset, normalized to a maximum of 1 and averaged for a variety of thicknesses of the top two tissue layers.

Materials and Methods
  SORS Probe Design:
  The primary criterion for designing a SORS probe for breast tumor margin analysis was to ensure proper depth sampling—that is, to develop a probe sensitive to tumor spectral signatures if the tumor is anywhere within the first 2 mm in depth from the excised surface. From the previous experimental [22] and simulation [18] results, a range of S-D offsets from 0.5 to 3.5 mm is appropriate to sample breast tissue from the surface to 2 mm below the surface. Another factor to consider given this range of offsets was the corresponding drop in SNR as S-D offset increases, since fewer photons can traverse long enough paths to reach the further offset detectors compared with closer offset detectors. To that end, SORS Monte Carlo simulations were run using the same model as for previous results [18]. Simulations were run for 3-layered samples, consisting of a top layer of 0.5 to 2 mm of normal breast tissue, a 0.1 to 20 mm thick middle layer of breast tumor, and then a 2 cm thick bottom layer of normal breast tissue to mimic the clinical situation of semi-infinite geometry. As a metric for SNR, the total number of Raman photons reaching each detector bin was counted and normalized to a maximum of 1, since we are only interested in how SNR falls off with S-D offset. FIG. 11 shows the mean of these curves; since the standard deviation was less than 1% over the range of thicknesses for the top two layers, no error bars are shown. As expected, the number of Raman photons detected fell off at an exponential decay as a function of S-D offset.

The above results were used to aid the design of a multi-separation SORS probe (assembled by EMVision, Loxahatchee, Fla.), whose distal tip is shown in FIG. 12. A single 400 µm diameter source, or excitation fiber is found on one end, and four (partial) rings of 300 µm diameter collection fibers extend radially outward. The excitation fiber includes a bandpass filter at its tip to clean up the laser line, and the collection fibers have longpass filters at their tips to reject elastically scattered light. The center to center distances of the excitation fiber to each detection ring are 0.5 mm, 1.5 mm, 2.5 mm and 3.5 mm. Based on FIG. 11, an additional collection fiber was added to each consecutive detector ring to make the SNRs from each ring more comparable. While the curve in FIG. 11 is not linear, adding a single fiber between each ring provided the closest approximation of equivalent SNRs if all of the fibers in each ring were binned. Adding a fiber in each successive detector ring had an added benefit of increasing the sampling volume of the probe as well.

Instrumentation and Data Processing:
The SORS probe delivered 80 mW of power from a 785 nm diode laser (Innovative Photonics Solutions, Monmouth Junction, N.J.). The collection fibers delivered light to a NIR-optimized spectrograph (Princeton Instruments, Princeton, N.J.), which dispersed the light to be recorded by a deep depletion, thermo-electrically cooled CCD (Princeton Instruments).

Each acquisition with the SORS probe recorded four spectra—one from each detector ring. Each ring was calibrated separately since the inherent curvature in the detection system created slight, but noticeable differences in peak locations on the CCD among different rings. A neon-argon lamp, naphthalene, and acetaminophen standards were used to calibrate the wavenumber axis, and a NIST-calibrated tungsten-halogen lamp was used to correct for the system response. After wavenumber binning and noise smoothing, the background fluorescence was subtracted with a modified polynomial fit algorithm [19], and the spectra were normalized according to their overall mean intensities. To create a composite spectrum with equal weighting from all four rings, which would contain information from the entire 2 mm sampling depth, the binned spectra from each of the four rings were averaged after processing.

SNR Testing:

To ensure the probe's ability to gather spectra from each ring with comparable SNRs, spectra were acquired for 20 seconds each from 12 different spots on a ~1 cm thick piece of chicken breast (muscle). The spectra were processed as described in section 2.2, and the SNR of the binned spectrum from each ring was calculated by dividing the height of the 1445 $cm^{-1}$ peak by the standard deviation of the flat spectral range between the 1656 and 1750 $cm^{-1}$ peaks.

In Vitro Sample Measurements:

With approval by the Vanderbilt Institutional Review Board (#050551) and the US Army Medical Research and Materiel Command's Human Research Protection Office (USAMRMC HRPO), fresh-frozen human breast tissue samples were acquired from the Cooperative Human Tissue Network. In total, 35 samples were included in the study; 15 samples had either no tumor or tumor>2 mm beneath normal tissue at the point of measurement and were thus labeled as "negative margins," while 20 samples had tumor regions within the first 2 mm from the measurement surface, and were thus labeled "positive margins." Wherever possible, measurements from tumor samples were taken such that the SORS probe was placed on a small region of visually normal-appearing tissue on top of the actual tumor to mimic the situation of margin evaluation. Spectra were recorded for 10-30 seconds and processed as above. Measurement sites were inked, fixed in formalin, and serially sectioned to correlate the spectra with histopathology diagnoses of tissue type and precise depths of those tissues. In this manner, the analysis was done to discriminate "negative" margins from "positive" margins.

Classification of Margin Status:

The composite spectrum from averaging all four detector rings was used for analysis, and if there were histological evidence of tumor cells within 2 mm of the measurement surface, the "margin" was considered positive. Discrimination was performed with sparse multinomial logistic regression (SMLR) [20], a Bayesian machine-learning framework that computes the posterior probability of a spectrum belonging to each tissue class based on a labeled training set. In the case of this binary analysis, whichever class had the higher probability of membership was the one to which the spectrum was classified. SMLR also includes inherent dimensionality reduction as it seeks to create sparse basis vectors, which is important for these data sets given their small sizes. Since each in vitro sample had only one measurement site, SMLR was run with leave-one-out cross-validation.

Results

Figure 13:
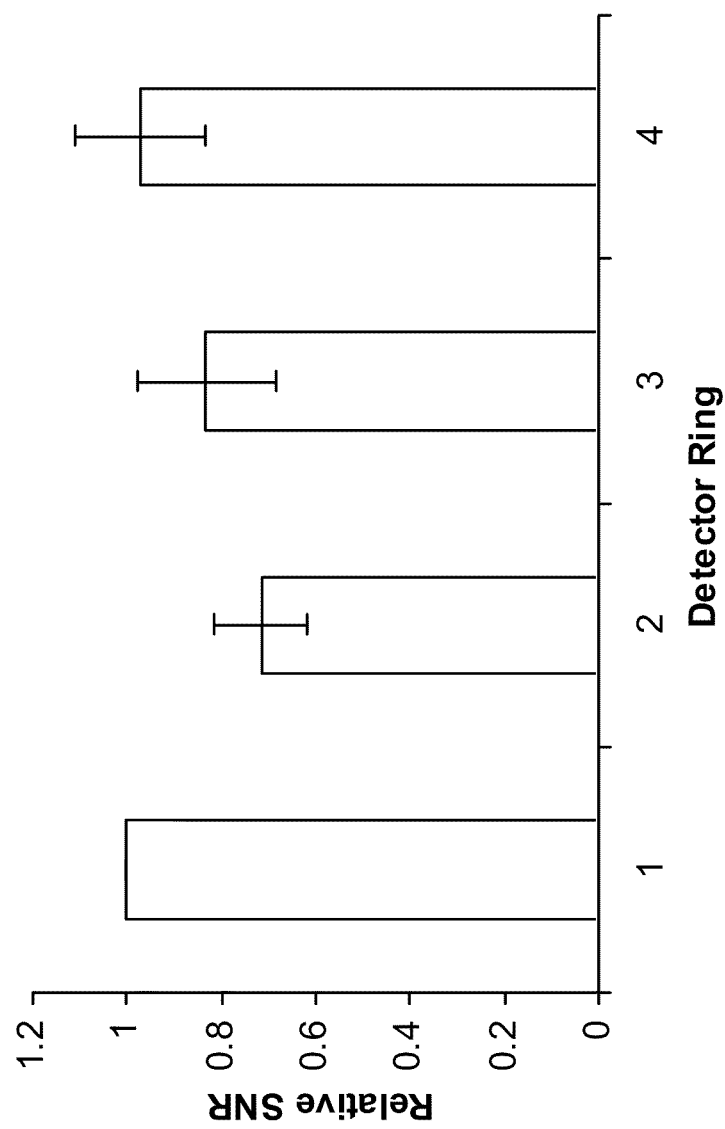
FIG. 13 shows mean (n=12) signal-to-noise ratios (SNR), plus or minus one standard deviation, for spectra of chicken muscle binned within each detector ring and normalized to SNR of first ring.

FIG. 13 shows the results of the SNR testing on chicken muscle. Rings 1 and 4 of the SORS probe, with one and four fibers per ring, and with S-D offsets of 0.5 and 3.5 mm, respectively, displayed nearly identical SNRs. Rings 2 and 3 showed smaller SNRs compared with Ring 1, but only by ~30% and 20%, respectively. This trend was expected based on the shape of FIG. 11, although the signal strengths of rings 2 and 3 were smaller than predicted by the simulations. The likely reason is that the detection fibers for the two middle rings were not able to be focused as tightly onto the CCD compared with the fibers for rings 1 and 4. Even so, the design of the SORS probe effectively accounted for SNR fall-off with increasing S-D offset.

Figure 14:
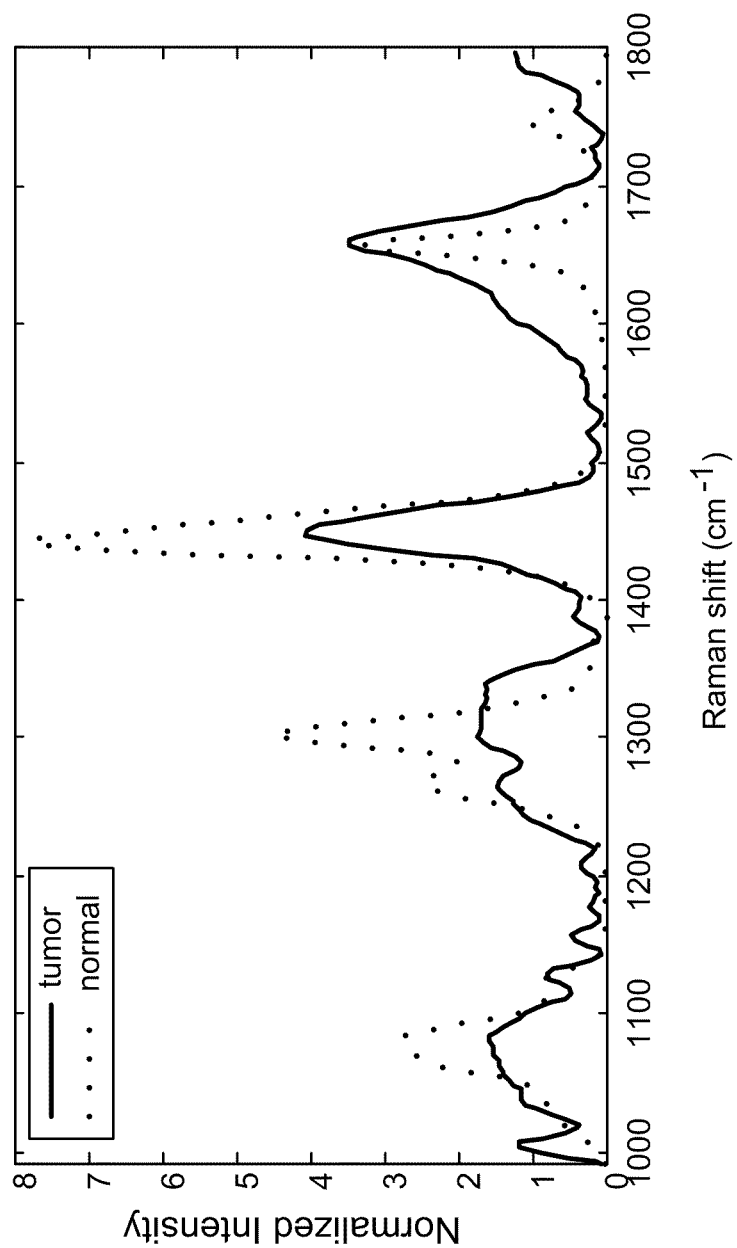
FIG. 14 shows typical composite spectra from SORS probe of normal breast tissue versus breast tumor (invasive ductal carcinoma) tissue.

FIG. 14 shows typical composite spectra recorded from pure normal breast tissue and pure breast tumor (invasive ductal carcinoma) tissue with the SORS probe. As in the previous study [22], there are numerous spectral regions with major differences between the two tissue types. In particular, tumor tissue contains a strong band at 1006 $cm^{-1}$, usually attributed to phenylalanine, while normal tissue does not. The ratios of the 1303 $cm^{-1}$ to 1265 $cm^{-1}$ bands, indicative of the ratio of lipid to protein content, are very different between the tissue types, and the amide I band centered around 1656 $cm^{-1}$ is much wider in tumor compared to normal—again indicative of increased protein contributions in the cancerous tissues. Also, the 1445 $cm^{-1}$ CH stretch band is relatively more intense in normal tissue, and the normal tissue contains a carbonyl stretch peak around 1750 $cm^{-1}$, typically due to fat content, while the tumor tissue does not.

Figure 15:
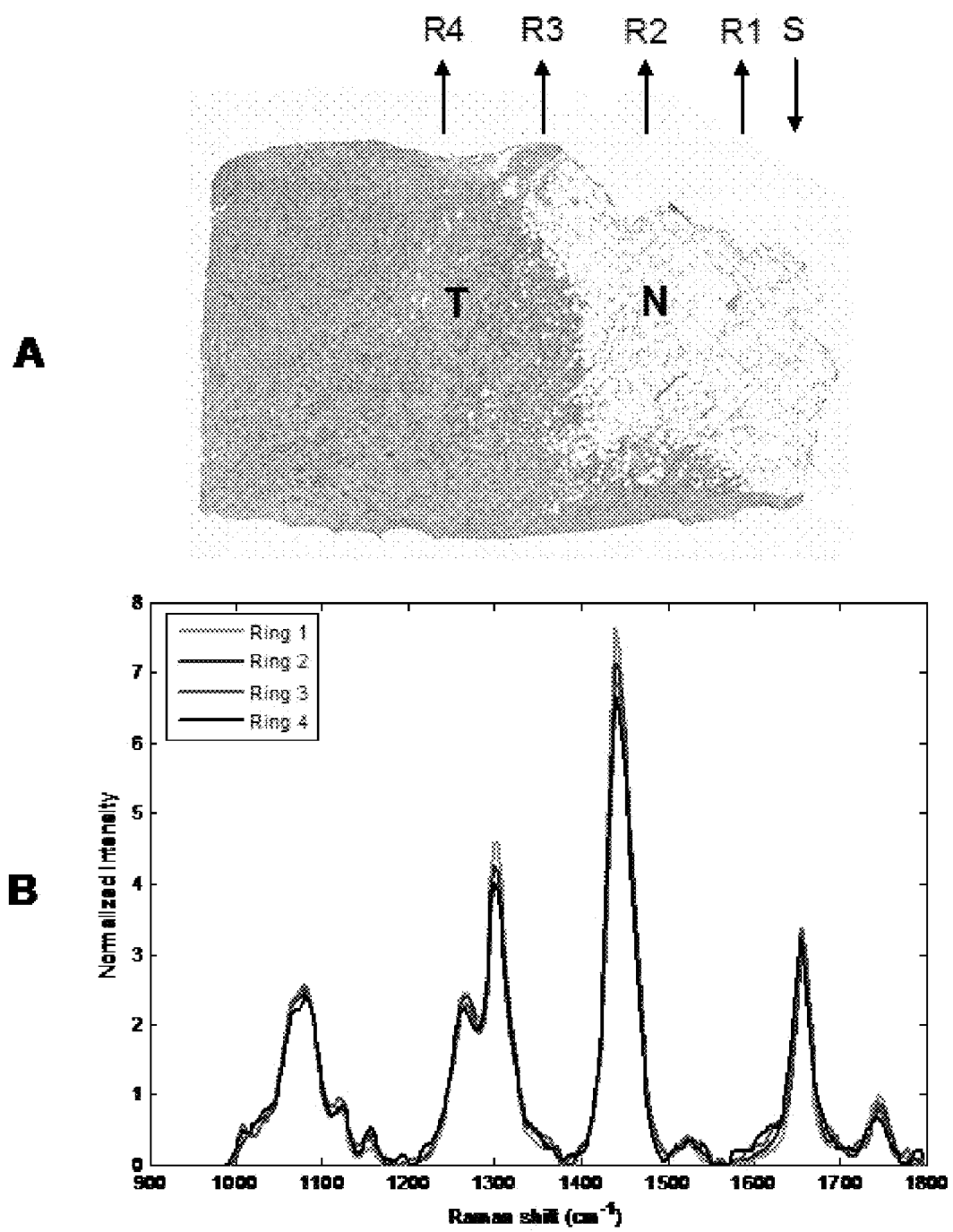
FIG. 15 shows (A) H&E stained tissue section of IDC sample with large area of normal fat (white colored area with "N") on the right, and solid IDC tumor (darkly stained area with "T") on the left. Arrows indicate the placement of the source fiber (S) and each of the detector rings. (B) Binned SORS spectra for each detector ring from tissue in A.
Figure 16:
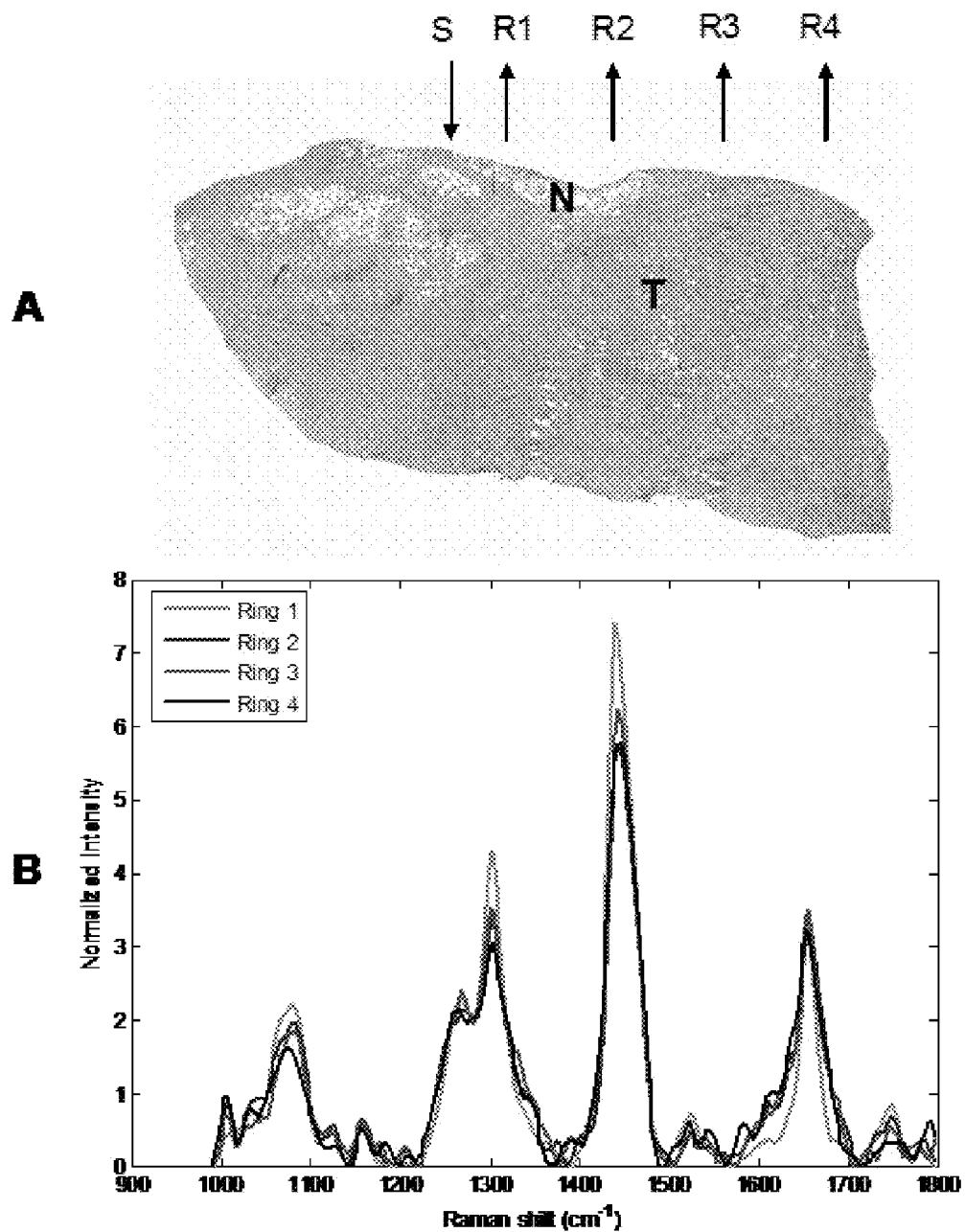
FIG. 16 shows (A) H&E stained tissue section of invasive lobular carcinoma sample with pockets of normal fat ("N") near surface of otherwise darkly stained tumor tissue ("T"). Arrows again represent placements of fibers. (B) SORS spectra for each detector ring from tissue in A.

FIGS. 15 and 16 show the H&E stained tissue section and the SORS spectra from that section from two in vitro tumor samples. In both FIGS. 5A and 6A, the "S" arrow indicates the placement of the source fiber, while "R1," "R2," etc. denote the location of the individual collection fiber rings. In the tissue sample from FIG. 15A, the probe was delivering light to a large fatty area, as seen by the whitish lipid-filled vacuoles, while only the outermost collection fibers were placed over a portion of the invasive ductal carcinoma (IDC) tumor, which comprises the remainder of the darkly stained section. Although spectral differences among detector rings in FIG. 15B are visually subtle, there are definite trends indicating that the closer rings are sampling normal tissue, while the outer rings are picking up slight spectral contributions from the tumor as well. By comparing the spectra in FIG. 15B with the pure normal and tumor spectra from FIG. 14, these trends are indicative of picking up some tumor signature, including the increasing presence of the 1006 $cm^{-1}$ peak, the lesser relative contributions from the 1303 and 1445 $cm^{-1}$ peaks, and the increasing width of the 1656 $cm^{-1}$ peak as source-detector offset increases. These trends are similar to those seen in the earlier report of SORS on layered breast tissues [22], but in this case, the tissue boundary was vertical rather than horizontal.

The example in FIG. 16 provides an illustration of what happens with smaller layers of normal tissue over a tumor. FIG. 16A shows an invasive lobular carcinoma (ILC) sample with pockets of normal adipose cells near the surface, including directly under the location where the excitation fiber from the probe was placed. From FIG. 16B, in comparison to FIG. 14, the spectrum from the smallest S-D offset contains mostly features indicative of normal fatty breast tissue, while spectra from the further S-D offsets contain features indicative of tumor spectral signatures, as noted above. Thus, it is clear that the different detector rings are sampling different volumes, as desired. Although not shown here, it was confirmed that if the probe were placed on tumor tissue overlying normal tissue (i.e. the opposite of margin analysis), then the inner detector rings picked up tumor signatures, while the outer rings picked up the appropriate degree of normal spectral signatures.

To simplify the "margin analysis" procedure, the spectra from each detector ring were averaged to create one composite spectrum per in vitro sample. Thus, a single histological classification could be correlated to a single spectral classification. Table 1 shows the confusion matrix for classification of these composite spectra with SMLR. This analysis showed an excellent ability for SORS to evaluate margin status in breast specimens, with 95% sensitivity and 100% specificity, and an area under the ROC curve of 0.993. Alternatively, the discrimination was performed with 94% negative predictive value (NPV) and 100% positive predictive value (PPV). The one false negative came from a tumor sample which, after formalin fixation and sectioning, was found to have a ~1.5 mm layer of normal tissue between the measurement site and the tumor. Since it has been shown that normal tissue margins tend to shrink by an average of 33% during formalin fixation [21], it is possible that this normal layer was at least 2 mm thick when the spectra were obtained.

TABLE 1

Confusion matrix for "margin analysis" on in vitro specimens.

| | | Spectral Margin Status | | |
| --- | --- | --- | --- | --- |
| | | Negative | Positive | |
| Histopathology | Negative | 15 | 0 | Specificity: 100% |
| Margin Status | Positive | 1 | 19 | Sensitivity: 95% |
| | | NPV: 94% | PPV: 100% | |

Discussion

This example presents the design, testing, and implementation of a multi-separation SORS probe for use in evaluating margin status following partial mastectomies. The design, as shown in FIG. 12, was based on results from our earlier experimental and simulation-based studies [22, 18], and from the SNR simulation results from FIG. 11. To ensure that the SNRs were comparable across the different detector rings, a series of measurements was performed using the common soft tissue optical phantom of chicken breast. As seen in FIG. 13, the design of adding an additional collection fiber for each further-offset ring worked well to keep the SNR of each ring no more than ~30% different from the others. Given the exponential shape of FIG. 11, it would be very difficult to design a probe to both sample the desired depths in tissue and achieve even better equilibration of SNR among the various detector rings. Besides the SNR balancing, the probe design from FIG. 12 also appeared to sample tissue to the expected depths based on earlier experimental [22] and simulation [18] results. This conclusion is supported by the success shown in Table 1 for classifying spectra according to margin status using 2 mm as the cutoff value for negative vs. positive.

The ability of the detector rings to sample different volumes is seen in FIGS. 5 and 6. From FIG. 15A, it is clear that the SORS probe was placed over two very different regions of tissue for that specimen. A very large area of normal fatty tissue was found directly under the excitation fiber and the first 2-3 detector rings, while the outermost 1-2 detector rings were placed against the tumor. Comparing FIG. 15B to the pure normal and fat spectra from FIG. 14, rings 1 and 2 show essentially no tumor spectral signatures. Given this, a standard Raman probe placed in the same spot would not detect any positive margin findings at this point. The $3^{rd}$ and $4^{th}$ rings of the probe were able to pick up slight tumor contributions though, indicating that they successfully sampled a different volume of tissue than the inner rings. A similar situation was seen in FIG. 16, although there, only the first detector ring was sensitive to a small (<1 mm thick) fat layer on the surface, while the outer rings sampled deeper/more radially distal tissue volumes. It should be noted that in the processing of samples, the fat regions tend to shrink [21], so the measurement surface of that specimen was likely much more level during signal acquisition. Also, the specimen was cut after fixation and before sectioning to make the given section contain only the interrogated tissue region, so the fibers were never placed over the very edge of any sample.

Given these findings regarding sampling depths and volumes, it was decided to use the composite spectra for margin analysis on intact breast specimens in the laboratory. Since the SNR is approximately equal in all four rings (see FIG. 13), averaging them provides information about the entire sampling volume in a single spectrum. This method also simplifies the analysis procedure; if spectra from individual rings were used, it would be difficult to determine how to correlate certain ones with pathology findings. For example, although all spectra in FIGS. 5B and 6B were from tissue sites that would be deemed positive margins within the spatial extent of the probe, it is unlikely that the innermost rings were actually picking up any signal from tumor tissues. A possible approach for using the individual spectra would be to label a measurement site "positive" if any spectrum from the four rings is predicted to be from a positive margin, but the aforementioned correlation issue arises in the training of such an algorithm for a retrospective analysis. Many normal-looking spectra, like ring 1 from FIG. 15B, would be labeled as tumor and would likely cause difficulties for discrimination algorithms trying to create decision boundaries between negative and positive margins.

The results from using SMLR to classify the composite SORS spectra according to margin status are shown in Table 1. With only one false negative, the sensitivity, specificity, NPV, and PPV were all at least 94%, which compares extremely favorably with current intraoperative margin evaluation techniques [5-7]. For this clinical application, perhaps the most important variable is NPV, since a surgeon needs to be confident in any diagnosis of negative margin status to prevent recurrence of the disease or unnecessary second operations. For the single false negative result in this study, the normal layer overlying the tumor was found to be ~1.5 mm thick upon histological examination, but prior to formalin fixation, this layer was likely around or slightly greater than 2 mm thick [21], which would surpass the sampling capabilities of the SORS probe. In addition, there is not a universal standard among hospitals of minimum margin size required during breast conserving surgery; rather, some locations use 2 mm, some use 1 mm, and others simply require that no cancer cells be found on the surface of the specimen [3]. We used 2 mm as the cutoff in this study because that value provides the best prognosis for patients [3] and is the most stringent standard for proving the value of SORS.

Although this analysis was performed on a fairly small sample size, it was still well-powered at the 95% level. A simpler binary diagnostic algorithm may seem like a more appropriate approach in this analysis, but the SMLR algorithm was able to significantly reduce the dimensionality of the data from the initial size of 232 variables (one per wavenumber) to perform its classification. In addition, SMLR provides a probability of class membership that would be very useful in a clinical application. A surgeon could act differently if the probability of a margin being negative is 99% versus 51%, although in either case, the diagnosis would be "negative."

While it may not be possible to state broad, sweeping conclusions from this work's sample sizes, it has demonstrated the feasibility and promise of using SORS to evaluate margin status on intact breast specimens in a laboratory setting. Studies are currently underway on using the same approach in a clinical setting; initial results are equally as promising as the laboratory measurements, and these clinical SORS measurements for breast tumor surgical margin evaluation will be the subject of future manuscripts.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments can become apparent to those skilled in the art to which the present invention pertains without departing from its spirit and scope. Accordingly, the scope of the present invention is defined by the entire disclosure including the description above, the appended claims, attached drawings, and appendices A and B, all of which are integral parts of this application.

REFERENCES

[1]. L. M. Moreira, L. Silveira, F. V. Santos, J. P. Lyon, R. Rocha, R. A. Zangaro, A. B. Villayerde, and M. T. T. Pacheco, "Raman spectroscopy: A powerful technique for biochemical analysis and diagnosis," Spectr.-Int. J. 22, 1-19 (2008).

[2]. M. D. Keller, E. M. Kanter, and A. Mahadevan-Jansen, "Raman spectroscopy for cancer diagnosis," Spectroscopy 21, 33-41 (2006).

[3]. U. Utzinger and R. R. Richards-Kortum, "Fiber optic probes for biomedical optical spectroscopy," J Biomed Opt 8, 121-147 (2003).

[4]. P. Matousek, I. P. Clark, E. R. Draper, M. D. Morris, A. E. Goodship, N. Everall, M. Towrie, W. F. Finney, and A. W. Parker, "Subsurface probing in diffusely scattering media using spatially offset Raman spectroscopy," Appl Spectrosc 59, 393-400 (2005).

[5]. P. Matousek, E. R. Draper, A. E. Goodship, I. P. Clark, K. L. Ronayne, and A. W. Parker, "Noninvasive Raman spectroscopy of human tissue in vivo," Appl Spectrosc 60, 758-763 (2006).

[6]. M. V. Schulmerich, K. A. Dooley, M. D. Morris, T. M. Vanasse, and S. A. Goldstein, "Transcutaneous fiber optic Raman spectroscopy of bone using annular illumination and a circular array of collection fibers," J Biomed Opt 11, 060502 (2006).

[7]. N. Stone, R. Baker, K. Rogers, A. W. Parker, and P. Matousek, "Subsurface probing of calcifications with spatially offset Raman spectroscopy (SORS): future possibilities for the diagnosis of breast cancer," Analyst 132, 899-905 (2007).

[8]. N. A. Macleod, A. Goodship, A. W. Parker, and P. Matousek, "Prediction of sublayer depth in turbid media using spatially offset Raman spectroscopy," Analytical chemistry 80, 8146-8152 (2008).

[9]. E. B. C. T. C. Group, "Effects of radiotherapy and surgery in early breast cancer. An overview of the randomized trials," N Engl J Med 333, 1444-1455 (1995).

[10]. G. C. Balch, S. K. Mithani, J. F. Simpson, and M. C. Kelley, "Accuracy of intraoperative gross examination of surgical margin status in women undergoing partial mastectomy for breast malignancy," Am Surg 71, 22-27; discussion 27-28 (2005).

[11]. N. Cabioglu, K. K. Hunt, A. A. Sahin, H. M. Kuerer, G. V. Babiera, S. E. Singletary, G. J. Whitman, M. I. Ross, F. C. Ames, B. W. Feig, T. A. Buchholz, and F. Meric-Bernstam, "Role for intraoperative margin assessment in patients undergoing breast-conserving surgery," Ann Surg Oncol 14, 1458-1471 (2007).

[12]. C. M. Krishna, J. Kurien, S. Mathew, L. Rao, K. Maheedhar, K. K. Kumar, and M. Chowdary, "Raman spectroscopy of breast tissues," Expert Rev Mol Diagn 8, 149-166 (2008).

[13]. S. K. Majumder, M. D. Keller, M. C. Kelley, F. I. Boulos, and A. Mahadevan-Jansen, "Comparison of autofluorescence, diffuse reflectance, and Raman spectroscopy for breast tissue discrimination," J Biomed Optics 13, 054009 (2008).

[14]. A. S. Haka, Z. Volynskaya, J. A. Gardecki, J. Nazemi, J. Lyons, D. Hicks, M. Fitzmaurice, R. R. Dasari, J. P. Crowe, and M. S. Feld, "In vivo margin assessment during partial mastectomy breast surgery using raman spectroscopy," Cancer Res 66, 3317-3322 (2006).

[15]. C. A. Lieber and A. Mahadevan-Jansen, "Automated method for subtraction of fluorescence from biological Raman spectra," Appl Spectrosc 57, 1363-1367 (2003).

[16]. M. V. Schulmerich, K. A. Dooley, M. D. Morris, T. M. Vanasse and S. A. Goldstein, "Transcutaneous fiber optic Raman spectroscopy of bone using annular illumination and a circular array of collection fibers," Journal of biomedical optics 11(6), 060502 (2006).

[17]. P. Matousek, E. R. Draper, A. E. Goodship, I. P. Clark, K. L. Ronayne and A. W. Parker, "Noninvasive Raman spectroscopy of human tissue in vivo," Appl Spectrosc 60(7), 758-763 (2006).

[18]. M. D. Keller, R. H. Wilson, M.-A. Mycek and A. Mahadevan-Jansen, "Numerical simulations of spatially offset Raman spectroscopy for breast tumor margin analysis," Optics express (in preparation).

[19]. C. A. Lieber and A. Mahadevan-Jansen, "Automated method for subtraction of fluorescence from biological Raman spectra," Appl Spectrosc 57(11), 1363-1367 (2003).

[20]. B. Krishnapuram, L. Carin, M. A. T. Figueiredo and A. J. Hartemink, "Sparse multinomial logistic regression: Fast algorithms and generalization bounds," Ieee Transactions on Pattern Analysis and Machine Intelligence 27(6), 957-968 (2005).

[21]. B. H. Yeap, S. Muniandy, S. K. Lee, S. Sabaratnam and M. Singh, "Specimen shrinkage and its influence on margin assessment in breast cancer," Asian journal of surgery/Asian Surgical Association 30(3), 183-187 (2007).

[22]. M. D. Keller, S. K. Majumder and A. Mahadevan-Jansen, "Spatially offset Raman spectroscopy of layered soft tissues," Opt Lett 34(7), 926-928 (2009).

What is claimed is:

1. A method for surgical margin evaluation of tissues at a surgical site of interest, comprising the steps of:
    (a) illuminating the surgical site at at least one first spot with light, by a probe;
    (b) collecting Raman scattering light from the surgical site at a plurality of second spots, respectively, in response to illumination by the light, by the probe, wherein each second spot is apart from the at least one first spot so as to define a source-detection (S-D) offset distance between the at least one first spot illuminated with the light and said second spot from which the Raman scattering light is collected, wherein the plurality of second spots is located such that the S-D offset distance between the at least one first spot and a j-th second spot is j×d2, j=1, 2, 3, ... M, M being the number of the plurality of second spots and d2 being a constant, and wherein the probe has a working end configured such that the light is delivered to the at least one first spot, and the Raman scattering light is collected from the plurality of second spots;

(c) obtaining the plurality of spatially offset Raman spectra from the collected Raman scattering light, by a detector coupled with the probe, wherein each spatially offset Raman spectrum is corresponding to a respective second spot of the surgical site, and associated with a depth of the tissues at which the Raman light is scattered;

(d) acquiring a Raman spectrum from the at least one first spot illuminated with the light;

(e) identifying tissue signatures from the plurality of spatially offset Raman spectra; and (f) determining surgical margin status of the surgical site from the identified tissue signatures, wherein the identifying step comprises the step of comparing each of the Raman spectrum acquired from the at least one first spot and the plurality of spatially offset Raman spectra with a standard Raman spectrum of tumor tissues so as to determine a tumor signature of the corresponding Raman spectrum; and wherein the comparing step comprises the steps of:

(A) identifying spectral peaks of one of the plurality of spatially offset Raman spectra at a corresponding S-D offset distance between the at least one first spot and a second spot from which the one of the plurality of spatially offset Raman scattering light is collected;

(B) calculating the tumor signature, $\{T(i)\}$, for each identified peak of the one of the plurality of spatially offset Raman spectra at the corresponding S-D offset distance:

$$T(i)=[I_{SD}(i)-I_N(i)]/[I_{tumor}(i)-I_N(i)),$$

wherein i=1, 2, ..., N, N being the number of the spectral peaks, wherein $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively;

(C) averaging the tumor signature $\{T(i)\}$ for the N spectral peaks of the one of the plurality of spatially offset Raman spectra to obtain an overall relative tumor contribution in the one of the plurality of spatially offset Raman spectra; and (D) repeating steps (A)-(C) for the rest of the plurality of spatially offset Raman spectra.

2. The method of claim 1, wherein the S-D offset distance is smaller than 50 mm.

3. The method of claim 1, wherein the light illuminating the surgical site is a coherent light generated from a laser.

4. The method of claim 1, wherein the detector comprises at least one of a spectrograph and a CCD camera.

5. The method of claim 1, wherein the probe has in-line filters placed on the working end.

6. The method of claim 1, wherein the probe comprises:
at least one first fiber positioned over the at least one first spot of the surgical site for delivering the light thereto; and
at least one second fiber positioned over the surgical site and translationally movable from one to another of the plurality of second spots for collecting the Raman scattering light therefrom.

7. The method of claim 1, wherein the probe comprises:
at least one first fiber positioned over the at least one first spot of the surgical site for delivering the light thereto; and
a plurality of second fibers spatially arranged surrounding the at least one first fiber, each second fiber adapted for collecting the Raman scattering light from a corresponding second spot.

8. The method of claim 1, wherein the probe comprises a fiber array having:
at least one first fiber; and
a plurality of second fibers, wherein the at least one first fiber and the plurality of second fibers spatially arranged in a row or in a matrix form, wherein the at least one first fiber is adapted for delivering the light to the at least one first spot of the surgical site, and wherein the plurality of second fibers is adapted for collecting the Raman scattering light from the plurality of second spots of the surgical site.

9. The method of claim 1, wherein the probe comprises a fiber array having:
at least one first fiber; and
a plurality of second fibers spatially arranged in a radial ring form originated from the at least one first fiber, wherein the at least one first fiber is adapted for delivering the light to the at least one first spot of the surgical site, and wherein plurality of second fibers is adapted for collecting the Raman scattering light from the plurality of second spots of the surgical site.

10. The method of claim 1, wherein the determining step comprises the step of determining the tissues that produce the more than one peak in a normalized intensity spectrum as the tissues having a layered structure.

11. The method of claim 10, wherein the tissues comprises at least a first type of tissues and second type of tissues, wherein the first type of tissues comprise normal tissues, and the second type of tissues comprise cancer tissues.

12. A system for surgical margin evaluation of tissues at a surgical site of interest, comprising:
(a) a laser for emitting a coherent light;
(b) a probe having a working end, coupled with the light source and for delivering the coherent light to the surgical site to illuminate at at least one first spot proximal to the working end, and collecting from the working end Raman scattering light scattered from the surgical site at a plurality of second spots, respectively, in response to illumination by the coherent light, wherein each second spot is apart from the at least one first spot so as to define a source-detection (S-D) offset distance between the at least one first spot illuminated with the light and said second spot from which the Raman scattering light is collected, wherein the plurality of second spots is located such that the S-D offset distance between the at least one first spot and a j-th second spot is j×d2, j=1, 2, 3, ... M, M being the number of the plurality of second spots and d2 being a constant, and wherein the probe has a working end configured such that the light is delivered to the at least one first spot, and the Raman scattering light is collected from the plurality of second spots;
(c) a detector coupled with the probe for obtaining a plurality of spatially offset Raman spectra from the collected Raman scattering light and a Raman spectrum from the at least one first spot illuminated with the light, wherein each spatially offset Raman spectrum is corresponding to a respective second spot of the surgical site, and associated with a depth of the tissues at which the Raman light is scattered, and wherein the detector comprises at least one of a spectrograph and a CCD camera; and (d) a processor coupled with the detector and programmed to compare each of the Raman spectrum acquired from the at least one first spot and the plurality of spatially offset Raman spectra with a standard Raman spectrum of tumor tissues so as to identify tissue signatures from the plurality of spatially offset Raman spectra and the Raman spectrum at the at least one first spot; and determine surgical margins of the surgical site from the identified tissue signatures, wherein the comparison of each of the Raman spectrum acquired from the at least one first spot and the plurality of spatially offset Raman spectra with the standard Raman spectrum of tumor tissues is performed with the steps of:

(A) identifying spectral peaks of one of the plurality of spatially offset Raman spectra at the corresponding S-D offset distance between the at least one first spot and a second spot from which the one of the plurality of spatially offset Raman scattering light is collected;

(B) calculating the tumor signature, $\{T(i)\}$, for each identified peak of the one of the plurality of spatially offset Raman spectra at the corresponding S-D offset distance:

$$T(i)=[I_{SD}(i)-I_N(i)]/[I_{tumor}(i)-I_N(i)],$$

wherein i=1, 2, . . . , N, N being the number of the spectral peaks, wherein $I_{SD}(i)$, $I_N(i)$ and $I_{tumor}(i)$ are intensities of the i-th spectral peak of the one of the plurality of spatially offset Raman spectra, a standard Raman spectrum of normal tissues and the standard Raman spectrum of tumor tissues, respectively;

(C) averaging the tumor signature $\{T(i)\}$ for the N spectral peaks of the one of the plurality of spatially offset Raman spectra to obtain an overall relative tumor contribution in the one of the plurality of spatially offset Raman spectra; and (D) repeating steps (A)-(C) for the rest of the plurality of spatially offset Raman spectra.

13. The system of claim 12, wherein the S-D offset distance is smaller than 50 mm.

14. The system of claim 12, wherein the at least one first spot comprises a plurality of first spots, and wherein the number of the plurality of first spots is smaller than the number of the plurality of second spots.

15. The system of claim 12, further comprising in-line filters placed on the working end of the probe.

16. The system of claim 12, wherein the probe comprises:
at least one first fiber positioned over the at least one first spot of the surgical site for delivering the light thereto; and
at least one second fiber positioned over the surgical site and translationally movable from one to another of the plurality of second spots for collecting the Raman scattering light therefrom.

17. The system of claim 12, wherein the probe comprises:
at least one first fiber positioned over the at least one first spot of the surgical site for delivering the light thereto; and
a plurality of second fibers spatially arranged surrounding the at least one first fiber, each second fiber adapted for collecting the Raman scattering light from a corresponding second spot.

18. The system of claim 12, wherein the probe comprises a fiber array having:
at least one first fiber; and
a plurality of second fibers, wherein the at least one first fiber and the plurality of second fibers spatially arranged in a row or in a matrix form, wherein the at least one first fiber is adapted for delivering the light to the at least one first spot of the surgical site, and wherein plurality of second fibers is adapted for collecting the Raman scattering light from the plurality of second spots of the surgical site.

19. The system of claim 12, wherein the probe comprises a fiber array having:
at least one first fiber; and
a plurality of second fibers spatially arranged in a radial ring form originated from the at least one first fiber, wherein the at least one first fiber is adapted for delivering the light to the at least one first spot of the surgical site, and wherein the plurality of second fibers is adapted for collecting the Raman scattering light from the plurality of second spots of the surgical site.

20. The system of claim 12, wherein the processor is programmed to perform the step of comparing each of the Raman spectrum acquired from the at least one first spot and the plurality of spatially offset Raman spectra with a standard Raman spectrum of tumor tissues so as to determine a tumor signature of the corresponding Raman spectrum.

21. The system of claim 12, wherein the processor is programmed to perform the step of determining the tissues that produce the more than one peak in a normalized intensity spectrum as the tissues having a layered structure.

22. The system of claim 21, wherein the tissues comprises at least a first type of tissues and a second type of tissues, wherein the first type of tissues comprise normal tissues, and the second type of tissues comprise cancer tissues.

* * * * *